US008926985B2

(12) United States Patent
Capiau et al.

(10) Patent No.: US 8,926,985 B2
(45) Date of Patent: Jan. 6, 2015

(54) VACCINE

(75) Inventors: Carine Capiau, Rixensart (BE); Marguerite Deschamps, Rixensart (BE); Pierre Michel Desmons, Rixensart (BE); Craig Antonyjoseph Laferriere, Rixensart (BE); Jan Poolman, Rixensart (BE); Jean-Paul Prieels, Rixensart (BE)

(73) Assignee: GlaxoSmithKline Biologicals S A, Rixensart (BE)

( * ) Notice: Subject to any disclaimer, the term of this patent is extended or adjusted under 35 U.S.C. 154(b) by 230 days.

(21) Appl. No.: 12/612,988

(22) Filed: Nov. 5, 2009

(65) Prior Publication Data

US 2010/0119544 A1 May 13, 2010

Related U.S. Application Data

(63) Continuation of application No. 10/929,042, filed on Aug. 27, 2004, now abandoned, which is a continuation of application No. 09/914,518, filed as application No. PCT/EP00/02468 on Mar. 17, 2000, now abandoned.

(30) Foreign Application Priority Data

| Mar. 19, 1999 | (GB) | 9906437.0 |
| Apr. 20, 1999 | (GB) | 9909077.1 |
| Apr. 23, 1999 | (GB) | 9909466.6 |
| Jul. 15, 1999 | (GB) | 9916677.9 |

(51) Int. Cl.

| A61K 39/385 | (2006.01) |
| A61K 39/116 | (2006.01) |
| A61K 39/00  | (2006.01) |
| A61K 39/02  | (2006.01) |
| A61K 39/09  | (2006.01) |
| A61K 39/102 | (2006.01) |
| A01N 43/04  | (2006.01) |
| C07H 1/00   | (2006.01) |
| A61K 39/095 | (2006.01) |
| A61K 39/155 | (2006.01) |

(52) U.S. Cl.
CPC ....... A61K 39/155 (2013.01); *A61K 2039/6037* (2013.01); *A61K 2039/6075* (2013.01); *A61K 2039/55505* (2013.01); *A61K 2039/6068* (2013.01); *A61K 2039/55572* (2013.01); A61K 39/102 (2013.01); A61K 39/095 (2013.01); A61K 39/092 (2013.01); *Y10S 424/831* (2013.01)
USPC ............... 424/197.11; 424/203.1; 424/244.1; 424/234.1; 424/831; 424/256.1; 514/23; 536/123.1

(58) Field of Classification Search
None
See application file for complete search history.

(56) References Cited

U.S. PATENT DOCUMENTS

| 6,224,880 B1 | 5/2001 | Chan et al. |
| 6,709,658 B1 | 3/2004 | LaPosta et al. |
| 2004/0228879 A1* | 11/2004 | Deschamps et al. ....... 424/211.1 |
| 2005/0031638 A1* | 2/2005 | Dalemans et al. ......... 424/186.1 |

FOREIGN PATENT DOCUMENTS

| EP | 0 594 610  | 5/1994 |
| WO | 90/06951   | 6/1990 |
| WO | WO9632963  | 10/1996 |
| WO | WO9633739  | 10/1996 |
| WO | WO9640242  | 12/1996 |
| WO | WO9735613  | 10/1997 |
| WO | WO9933488  | 7/1999 |
| WO | 00/10599   | 3/2000 |
| WO | 00/56359   | 9/2000 |
| WO | 00/56360   | 9/2000 |

OTHER PUBLICATIONS

Bixler et al. Adv. Exp. Med. Biol. 303: 185-190, 1991, abstract.*
Eskola, et al., *Reactogenicity and Immunogenicity of Combined Vaccines for Bacteraemic Diseases Caused by Haemophilus influenzae Type B, Meningococci and Pneumococci in 24-Month-Old children*, Vaccine, vol. 8(2): 107-110 (Apr. 1990).
Verheul, et al., *Meningococcal Lipopolysaccharides Virulence Factor and Potential Vaccine Component*, Microbiological Reviews, vol. 57(1): 34-49 (1993).
Alexander, et al., *Immunization of Mice with Pneumolysin Toxoid Confers a Significant Degree of Protection Against At Least Nine Serotypes of Streptococcus pneumoniae*, Infection & Immunity, vol. 62(12): 5683-5688 (1994).
De Velasco, et al., *Synthetic Peptides Representing T-Cell Epitopes Act as Carriers in Pneumococcal Polysaccharide Conjugate Vaccines*, Infection & Immunity, vol. 63(3): 961-968 (1995).
Akkoyunlu, Mustafa et al., *Biological Activity of Serum Antibodies to a Nonacylated Form of Lipoprotein D of Haemophilus influenzae*, Infection & Immunity, vol. 64(11): 4586-4592 (1996).
Lee, et al., *Immunologic Epitope Gene, and Immunity Involved in Pneumococcal Glycoconjugate*, Critical Reviews in Microbiology, vol. 23(2): 121-142 (1997).
Chu, et al., *CpG Oligodeoxynucleotides Act as Adjuvants that Switch on T Helper 1 (Th1) Immunity*, J. Exp. Med., vol. 186(10): 1623-1631 (1997).
Akkoyunlu, Mustafa et al., *The Acylated Form of Protein D of Haemophilus influenzae Is More Immunogenic than the Nonacylated Form and Elicits an Adjuvant Effect When It Is Used as a Carrier Conjugated to Polyribosyl Ribitol Phosphate*, Infection & Immunity, vol. 65(12): 5010-5016 (Dec. 1997).

(Continued)

Primary Examiner — S. Devi
(74) Attorney, Agent, or Firm — Alice P. Bradney

(57) ABSTRACT

The present invention relates to the field of bacterial polysaccharide antigen vaccines. In particular, the present invention relates to bacterial polysaccharides conjugated to protein D from *H. influenzae*.

12 Claims, 1 Drawing Sheet

(56) References Cited

OTHER PUBLICATIONS

Shams, et al., *The effect of conjugation on immunogenicity and potency of protein carriers of polyribosyl ribitol phosphate (PRP) conjugated vaccines in the mouse model*, APMIS, 106 & 526 (1998).

Briles, et al., *Pneumococcal Diversity: Considerations for New Vaccine Strategies with Emphasis on Pneumococcal Surface Protein A (PspA)*, Clinical Microbiology Reviews, vol. 11(4): 645-657 (Oct. 1998).

GlaxoSmithKline Response to European Patent Office dated Mar. 21, 2007, European Patent Application No. 00 912 626.9-2402.

U.S. Appl. No. 10/929,042, Office Action mailed May 5, 2009.

Janson, et al., Protein D, an Immunoglobulin D-binding protein of *Haemophilus influenzae*: Cloning, Nucleotide Sequence, and Expression in *Escherichia coli*, Infect & Immun 59(1):119-125 (1991).

Klein, Pneumococcal Conjugate Vaccines: Review and Update, Microbial Drug Resistance 1(1):49-58 (1995).

Gupta and Siber, Adjuvants for human vaccines—current status, problems and future prospects, Vaccine 13 (14):1263-1276 (1995).

Kensil, Saponins as Vaccine Adjuvants, Critical Reviews in Therapeutic Drug Carrier Systems 13(1&2):1-55 (1996).

Davis, et al., CpG DNA Is a Potent Enhancer of Specific Immunity in Mice Immunized with Recombinant Hepatitis B Surface Antigen, J Immunology 160(2):870-876 (1998).

Michon, et al., Multivalent pneumococcal capsular polysaccharide conjugate vaccines employing genetically detoxified pneumolysin as a carrier protein, Vaccine 16(18):1732-1741 (1998).

Klinman, et al., CpG motifs as immune adjuvants, Vaccine 17:19-25 (1999).

Qureshi, et al., Endotoxin-tolerant Mice Have Mutations in Toll-like Receptor 4 (Tlr4), J Exp Med 189(4):615-625 (1999).

\* cited by examiner

VACCINE

CROSS REFERENCE TO RELATED APPLICATIONS

This application is a Continuation of application Ser. No. 10/929,042, filed 27 Aug. 2004, now abandoned, which is a Continuation of application Ser. No. 09/914,518, filed 21 Dec. 2001, now abandoned, which is a national stage §371 application of International Application Number PCT/EP00/02468, filed 17 Mar. 2000, which claims the benefit of Great Britain Application Serial Number 9916677.9, filed 15 Jul. 1999, Great Britain Application Serial Number 9906437.0, filed 19 Mar. 1999, Great Britain Application Serial Number 9909077.1, filed 20 Apr. 1999, and Great Britain Application Serial Number 9909466.6, filed 23 Apr. 1999.

The entire contents of each of the foregoing applications are incorporated herein by reference.

FIELD OF INVENTION

The present invention relates to bacterial polysaccharide antigen vaccines, their manufacture and the use of such polysaccharides in medicines.

In particular the present invention relates to three inter-related aspects: A—vaccines comprising a pneumococcal polysaccharide antigen, typically a pneumococcal polysaccharide conjugate antigen, formulated with a protein antigen from *Streptococcus pneumoniae* and optionally a Th1 inducing adjuvant; B—specific, advantageous pneumococcal polysaccharide conjugates adjuvanted with a Th1 adjuvant; and C—bacterial polysaccharide conjugates in general conjugated to protein D from *H. influenzae*.

BACKGROUND OF INVENTION

*Streptococcus pneumoniae* is a Gram-positive bacteria responsible for considerable morbidity and mortality (particularly in the young and aged), causing invasive diseases such as pneumonia, bacteremia and meningitis, and diseases associated with colonisation, such as acute Otitis media. The rate of pneumococcal pneumonia in the US for persons over 60 years of age is estimated to be 3 to 8 per 100,000. In 20% of cases this leads to bacteremia, and other manifestations such as meningitis, with a mortality rate close to 30% even with antibiotic treatment.

Pneumococcus is encapsulated with a chemically linked polysaccharide which confers serotype specificity. There are 90 known serotypes of pneumococci, and the capsule is the principle virulence determinant for pneumococci, as the capsule not only protects the inner surface of the bacteria from complement, but is itself poorly immunogenic. Polysaccharides are T-independent antigens, and can not be processed or presented on MHC molecules to interact with T-cells. They can however, stimulate the immune system through an alternate mechanism which involves cross-linking of surface receptors on B cells.

It was shown in several experiments that protection against invasive pneumococci disease is correlated most strongly with antibody specific for the capsule, and the protection is serotype specific.

Polysaccharide antigen based vaccines are well known in the art. Four that have been licensed for human use include the Vi polysaccharide of *Salmonella typhi*, the PRP polysaccharide from *Haemophilus influenzae*, the tetravalent meningococcal vaccine composed of serotypes A, C, W135 and Y, and the 23-Valent pneumococcal vaccine composed of the polysaccharides corresponding to serotypes 1, 2, 3, 4, 5, 6B, 7F, 8, 9N, 9V, 10A, 11A, 12F, 14, 15B, 17F, 18C, 19A, 19F, 20, 22F, 23F, and 33 (accounting for at least 90% of pneumococcal blood isolates).

The latter three vaccines confer protection against bacteria causing respiratory infections resulting in severe morbidity and mortality in infants, yet these vaccines have not been licensed for use in children less than two years of age because they are inadequately immunogenic in this age group [Peltola et al. (1984), N. Engl. J. Med. 310:1561-1566]. *Streptococcus pneumoniae* is the most common cause of invasive bacterial disease and otitis media in infants and young children. Likewise, the elderly mount poor responses to pneumococcal vaccines [Roghmann et al., (1987), J. Gerontol. 42:265-270], hence the increased incidence of bacterial pneumonia in this population [Verghese and Berk, (1983) Medicine (Baltimore) 62:271-285].

Strategies, which have been designed to overcome this lack of immunogenicity in infants, include the linking of the polysaccharide to large immunogenic proteins, which provide bystander T-cell help and which induce immunological memory against the polysaccharide antigen to which it is conjugated. Pneumococcal glycoprotein conjugate vaccines are currently being evaluated for safety, immunogenicity and efficacy in various age groups.

A) Pneumococcal polysaccharide Vaccines

The 23-valent unconjugated pneumococcal vaccine has shown a wide variation in clinical efficacy, from 0% to 81% (Fedson et al. (1994) Arch Intern Med. 154: 2531-2535). The efficacy appears to be related to the risk group that is being immunised, such as the elderly, Hodgkin's disease, splenectomy, sickle cell disease and agammaglobulinemics (Fine et al. (1994) Arch Intern Med. 154:2666-2677), and also to the disease manifestation. The 23-valent vaccine does not demonstrate protection against pneumococcal pneumonia (in certain high risk groups such as the elderly) and otitis media diseases.

There is therefore a need for improved pneumococcal vaccine compositions, particularly ones which will be more effective in the prevention or amelioration of pneumococcal disease (particularly pneumonia) in the elderly and in young children.

The present invention provides such an improved vaccine.

B) Selected Pneumococcal Polysaccharide Conjugate+3D-MPL Compositions

It is generally accepted that the protective efficacy of the commercialised unconjugated pneumococcal vaccine is more or less related to the concentration of antibody induced upon vaccination; indeed, the 23 polysaccharides were accepted for licensure solely upon the immunogenicity of each component polysaccharide (Ed. Williams et al. New York Academy of Sciences 1995 pp. 241-249). Therefore further enhancement of antibody responses to the pneumococcal polysaccharides could increase the percentage of infants and elderly responding with protective levels of antibody to the first injection of polysaccharide or polysaccharide conjugate and could reduce the dosage and the number of injections required to induce protective immunity to infections caused by *Streptococcus pneumoniae*.

Since the early $20^{th}$ century, researchers have experimented with a huge number of compounds which can be added to antigens to improve their immunogenicity in vaccine compositions [reviewed in M. F. Powell & M. J. Newman, Plenum Press, NY, "Vaccine Design—the Subunit and Adjuvant Approach" (1995) Chapter 7 "A Compendium of Vaccine Adjuvants and Excipients"]. Many are very efficient, but cause significant local and systemic adverse reactions that preclude their use in human vaccine compositions. Aluminium-based adjuvants (such as alum, aluminium hydroxide or aluminium phosphate), first described in 1926, remain the only immunologic adjuvants used in human vaccines licensed in the United States.

Aluminium-based adjuvants are examples of the carrier class of adjuvant which works through the "depot effect" it induces. Antigen is adsorbed onto its surface and when the composition is injected the adjuvant and antigen do not immediately dissipate in the blood stream—instead the composition persists in the local environment of the injection and a more pronounced immune response results. Such carrier adjuvants have the additional known advantage of being suitable for stabilising antigens that are prone to breakdown, for instance some polysaccharide antigens.

3D-MPL is an example of a non-carrier adjuvant. Its full name is 3-O-deacylated monophosphoryl lipid A (or 3 De-O-acylated monophosphoryl lipid A or 3-O-desacyl-4' monophosphoryl lipid A) and is referred to as 3D-MPL to indicate that position 3 of the reducing end glucosamine is de-O-acylated. For its preparation, see GB 2220211 A. Chemically it is a mixture of 3-deacylated monophosphoryl lipid A with 4, 5 or 6 acylated chains. It was originally made in the early 1990's when the method to 3-O-deacylate the 4'-monophosphoryl derivative of lipid A (MPL) led to a molecule with further attenuated toxicity with no change in the immunostimulating activity.

3D-MPL has been used as an adjuvant either on its own or, preferentially, combined with a depot-type carrier adjuvant such as aluminium hydroxide, aluminium phosphate or oil-in-water emulsions. In such compositions antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1]. Such combinations are also preferred in the art for antigens that are prone to adsorption (for instance, bacterial polysaccharide conjugates), where adsorption onto alum tends to stabilise the antigen. Precipitated aluminium-based adjuvants are mostly used as they are the only adjuvants that are currently used in licensed human vaccines. Accordingly, vaccines containing 3D-MPL in combination with aluminium-based adjuvants are favoured in the art due to their ease of development and speed of introduction onto the market.

MPL (non 3-deacylated) has been evaluated as an adjuvant with several monovalent polysaccharide-conjugate vaccine antigens. Coinjection of MPL in saline enhanced the serum antibody response for four monovalent polysaccharide conjugates: pneumococcal PS 6B-tetanus toxoid, pneumococcal PS 12-diphtheria toxoid, and *S. aureus* type 5 and *S. aureus* type 8 conjugated to *Pseudomonas aeruginosa* exotoxin A [Schneerson et al. J. Immunology (1991) 147:2136-2140]. The enhanced responses were taught as being antigen-specific. MPL in an oil-in-water emulsion (a carrier type adjuvant) consistently enhanced the effect of MPL in saline due to the presence of MPL and antigen in the same particulate structure, and was considered to be the adjuvant system of choice for optimal delivery of other polysaccharide conjugate vaccines.

Devi et al. [Infect. Immun. (1991) 59:3700-7] evaluated the adjuvant effect of MPL (non 3-deacylated) in saline on the murine antibody response to a TT conjugate of *Cryptococcus neoformans* capsular polysaccharide. When MPL was used concurrently with the conjugate there was only a marginal increase in both the IgM- and IgG-specific response to the PS; however MPL had a much larger effect when administered 2 days after the conjugate. The practicality of using an immunization scheme that requires a delay in the administration of MPL relative to antigen, especially in infants, is questionable. The adjuvant effect of MPL with polysaccharides and polysaccharide-protein conjugates appears to be composition-dependent. Again, the incorporation of MPL in a suitable slow-release delivery systems (for instance using a carrier adjuvant) provides a more durable adjuvant effect and circumvents the problem of timing and delayed administration.

In summary, the state of the art has taught that, for particular polysaccharide or polysaccharide-conjugate antigens, where MPL or 3D-MPL is used as an adjuvant, it is advantageously used in conjunction with a carrier adjuvant (for instance the aluminium-based adjuvants) in order to maximise its immunostimulatory effect.

Surprisingly, the present inventors have found that for certain pneumococcal polysaccharide conjugates, the immunogenicity of the vaccine composition is significantly greater when the antigen is formulated with 3D-MPL alone rather than with 3D-MPL in conjunction with a carrier adjuvant (such as an aluminium-based adjuvant). Furthermore the observed improvement is independent of the concentration of 3D-MPL used, and whether the particular conjugates are in a monovalent composition or whether they are combined to form a polyvalent composition.

C) Bacterial Polysaccharide—Protein D Conjugates

As mentioned above, polysaccharide antigen based vaccines are well known in the art. The licensed polysaccharide vaccines mentioned above have different demonstrated clinical efficacy. The Vi polysaccharide vaccine has been estimated to have an efficacy between 55% and 77% in preventing culture confirmed typhoid fever (Plotkin and Cam, (1995) Arch Intern Med 155: 2293-99). The meningococcal C polysaccharide vaccine was shown to have an efficacy of 79% under epidemic conditions (De Wals P, et al. (1996) Bull World Health Organ. 74: 407-411). The 23-valent pneumococcal vaccine has shown a wide variation in clinical efficacy, from 0% to 81% (Fedson et al. (1994) Arch Intern Med. 154: 2531-2535). As mentioned above, it is accepted that the protective efficacy of the pneumococcal vaccine is more or less related to the concentration of antibody induced upon vaccination.

Amongst the problems associated with the polysaccharide approach to vaccination, is the fact that polysaccharides per se are poor immunogens. Strategies which have been designed to overcome this lack of immunogenicity include the linking of the polysaccharide to large highly immunogenic protein carriers, which provide bystander T-cell help.

Examples of these highly immunogenic carriers which are currently commonly used for the production of polysaccharide immunogens include the Diphtheria toxoid (DT or the CRM197 mutant), Tetanus toxoid (TT), Keyhole Limpet Haemocyanin (KLH), and the purified protein derivative of Tuberculin (PPD).

Problems Associated with Commonly-Used Carriers

A number of problems are associated with each of these commonly used carriers, including in production of GMP conjugates and also in immunological characteristics of the conjugates.

Despite the common use of these carriers and their success in the induction of anti polysaccharide antibody responses they are associated with several drawbacks. For example, it is known that antigen specific immune responses may be suppressed (epitope suppression) by the presence of preexisting antibodies directed against the carrier, in this case Tetanus toxin (Di John et al; (1989) Lancet, 2:1415-8). In the population at large, a very high percentage of people will have pre-existing immunity to both DT and TT as people are routinely vaccinated with these antigens. In the UK for example 95% of children receive the DTP vaccine comprising both DT and TT. Other authors have described the problem of epitope suppression to peptide vaccines in animal models (Sad et al, Immunology, 1991; 74:223-227; Schutze et al, J. Immunol. 135: 4, 1985; 2319-2322).

In addition, for vaccines which require regular boosting, the use of highly immunogenic carriers such as TT and DT are likely to suppress the polysaccharide antibody response after several injections. These multiple vaccinations may also be accompanied by undesirable reactions such as delayed type hyperresponsiveness (DTH).

KLH is known as potent immunogen and has already been used as a carrier for IgE peptides in human clinical trials. However, some adverse reactions (DTH-like reactions or IgE sensitisation) as well as antibody responses against antibody have been observed.

The selection of a carrier protein, therefore, for a polysaccharide based vaccine will require a balance between the necessity to use a carrier working in all patients (broad MHC recognition), the induction of high levels of anti-polysaccharide antibody responses and low antibody response against the carrier.

The carriers used previously for polysaccharide based vaccines, therefore have many disadvantages. This is particularly so in combination vaccines, where epitope suppression is especially problematic if the same carrier is used for various polysaccharide antigens. In WO 98/51339, multiple carriers in combination vaccines were used in order to try to get over this effect.

The present invention provides a new carrier for use in the preparation of polysaccharide/polypeptide-based immunogenic conjugates, that does not suffer from the aforementioned disadvantages.

The present invention provides a protein D (EP 0 594 610 B1) from *Haemophilus influenzae*, or fragments thereof, as a carrier for polysaccharide based immunogenic compositions, including vaccines. The use of this carrier is particularly advantageous in combination vaccines.

SUMMARY OF THE INVENTION

A) Pneumococcal Polysaccharide Vaccines

Accordingly the present invention provides a vaccine composition, comprising at least one *Streptococcus pneumoniae* polysaccharide antigen (preferably conjugated) and a *Streptococcus pneumoniae* protein antigen or immunologically functional equivalent thereof, optionally with a Th1 adjuvant (an adjuvant inducing a Th1 immune response). Preferably both a pneumococcal protein and Th1 adjuvant are included. The compositions of the invention are particularly suited in the treatment of elderly pneumonia.

Pneumococcal polysaccharide vaccines (conjugated or not) may not be able to protect against pneumonia in the elderly population for which the incidence of this disease is very high. The key defense mechanism against the pneumococcus is opsonophagocytosis (a humoral B-cell/neutrophil mediated event caused by the production of antibodies against the pneumococcal polysaccharide, the bacterium eventually becoming phagocytosed), however parts of the involved opsonic mechanisms are impaired in the elderly, i.e. superoxide production by PMN (polymorphonuclear cells), other reactive oxygen species production, mobilization of PMN, apoptosis of PMN, deformability of PMN. Antibody responses may also be impaired in the elderly.

Contrary to the normally accepted dogma, normal levels of anti-capsular polysaccharide antibodies may not be effective in complete clearance of bacteria, as pneumococci may invade host cells to evade this branch of the immune system.

Surprisingly, the present inventors have found that by simultaneously stimulating the cell mediated branch of the immune system (for instance T-cell meditated immunity) in addition to the humoral brach of the immune system (B-cell mediated), a synergy (or cooperation) results which is capable of enhancing the clearance of pneumococci from the host. This is a discovery which will aid the prevention (or treatment) of pneumococcal infection in general, but will be particularly important for the prevention (or treatment) of pneumonia in the elderly where polysaccharide based vaccines do not show efficacy.

The present inventors have found that both arms of the immune system may synergise in this way if a pneumococcal polysaccharide (preferably conjugated) is administered with a pneumococcal protein (preferably a protein expressed on the surface of pneumococci, or secreted or released, which can be processed and presented in the context of Class II and MHC class I on the surface of infected mammalian cells). Although a pneumococcal protein can trigger cell mediated immunity by itself, the inventors have also found that the presence of a Th1 inducing adjuvant in the vaccine formulation helps this arm of the immune system, and surprisingly further enhances the synergy between both arms of the immune system.

B) Selected Pneumococcal Polysaccharide Conjugate+3D-MPL Compositions

Accordingly, the present invention also provides an antigenic composition comprising one or more pneumococcal polysaccharide conjugates adjuvanted with 3D-MPL and substantially devoid of aluminium-based adjuvants, wherein at least one of the pneumococcal polysaccharide conjugates is significantly more immunogenic in compositions comprising 3D-MPL in comparison with compositions comprising 3D-MPL in conjunction with an aluminium-based adjuvant.

Preferred embodiments provided are antigenic compositions comprising conjugates of one or more of the following pneumococcal capsular polysaccharides: serotype 4, 6B, 18C, 19F, and 23F. In such compositions, each of the polysaccharides are surprisingly more immunogenic in compositions comprising 3D-MPL alone compared with compositions comprising 3D-MPL and an aluminium-based adjuvant.

Thus is one embodiment of the invention there is provided a antigenic composition comprising the *Streptococcus pneumoniae* capsular polysaccharide serotype 4, 6B, 18C, 19F or 23F conjugated to an immunogenic protein and 3D-MPL adjuvant, wherein the composition is substantially devoid of aluminium-based adjuvants.

In a second embodiment, the present invention provides a combination antigenic composition substantially devoid of aluminium-based adjuvants and comprising 3D-MPL adjuvant and two or more pneumococcal polysaccharide conjugates chosen from the group consisting of: serotype 4; serotype 6B; serotype 18C; serotype 19F; and serotype 23F.

C) Bacterial Polysaccharide—Protein D Conjugates

Accordingly, the present invention provides a polysaccharide conjugate antigen comprising a polysaccharide antigen derived from a pathogenic bacterium conjugated to protein D from *Haemophilus influenzae* or a protein D fragment thereof. In addition, the invention provides polyvalent vaccine compositions where one or more of the polysaccharide antigens are conjugated to protein D.

DESCRIPTION OF THE INVENTION

A) Pneumococcal Polysaccharide Vaccines

Figure 1A:
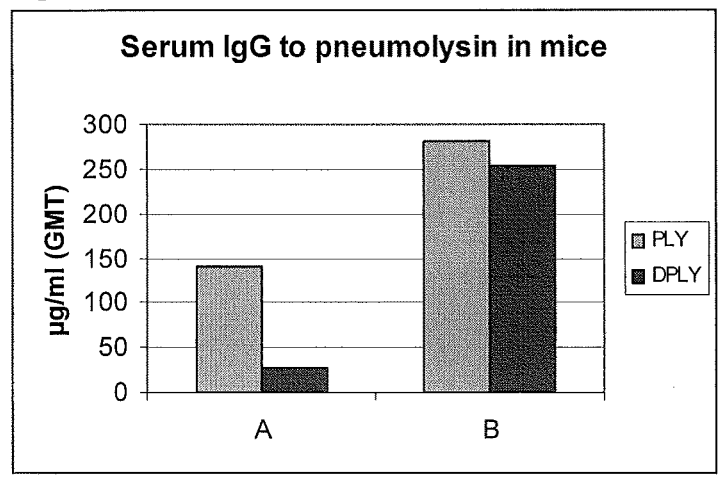
FIG. 1A: Serum IgG to pneumolysin in mice.

The present invention provides an improved vaccine particularly for the prevention or amelioration of pnemococcal infection of the elderly (and/or infants and toddlers).

In the context of the invention a patient is considered elderly if they are 55 years or over in age, typically over 60 years and more generally over 65 years.

Thus in one embodiment of the invention there is provided a vaccine composition, suitable for use in the elderly (and/or Infants and toddlers) comprising at least one *Streptococcus pneumoniae* polysaccharide antigen and at least one *Streptococcus pneumoniae* protein antigen.

In a second, preferred, embodiment, the present invention provides a vaccine (suitable for the prevention of pneumonia in the elderly) comprising at least one *Streptococcus pneumoniae* polysaccharide antigen and at least one *Streptococcus pneumoniae* protein antigen and a Th1 adjuvant.

It is envisaged that such a vaccine will be also useful in treating pneumococcal infection (for instance otitis media) in other high risk groups of the population, such as for infants or toddlers.

In a third embodiment there is provided a vaccine composition comprising a pneumococcal polysaccharide antigen and a Th1 adjuvant.

*Streptococcus pneumoniae* Polysaccharide Antigens of the Invention

Typically the *Streptococcus pneumoniae* vaccine of the present invention will comprise polysaccharide antigens (preferably conjugated), wherein the polysaccharides are derived from at least four serotypes of pneumococcus. Preferably the four serotypes include 6B, 14, 19F and 23F. More preferably, at least 7 serotypes are included in the composition, for example those derived from serotypes 4, 6B, 9V, 14, 18C, 19F, and 23F. More preferably still, at least 11 serotypes are included in the composition, for example the composition in one embodiment includes capsular polysaccharides derived from serotypes 1, 3, 4, 5, 6B, 7F, 9V, 14, 18C, 19F and 23F (preferably conjugated). In a preferred embodiment of the invention at least 13 polysaccharide antigens (preferably conjugated) are included, although further polysaccharide antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

For elderly vaccination (for instance for the prevention of pneumonia) it is advantageous to include serotypes 8 and 12F (and most preferably 15 and 22 as well) to the 11 valent antigenic composition described above to form a 15 valent vaccine, whereas for infants or toddlers (where otitis media is of more concern) serotypes 6A and 19A are advantageously included to form a 13 valent vaccine.

For the prevention/amelioration of pneumonia in the elderly (+55 years) population and Otitis media in Infants (up to 18 months) and toddlers (typically 18 months to 5 years), it is a preferred embodiment of the invention to combine a multivalent *Streptococcus pneumonia* polysaccharide as herein described with a *Streptococcus pneumoniae* protein or immunologically functional equivalent thereof.

Pneumococcal Proteins of the invention

For the purposes of this invention, "immunologically functional equivalent" is defined as a peptide of protein comprising at least one protective epitope from the proteins of the invention. Such epitopes are characteristically surface-exposed, highly conserved, and can elicit an bactericidal antibody response in a host or prevent toxic effects. Preferably, the functional equivalent has at least 15 and preferably 30 or more contiguous amino acids from the protein of the invention. Most preferably, fragments, deletions of the protein, such as transmembrane deletion variants thereof (ie the use of the extracellular domain of the proteins), fusions, chemically or genetically detoxified derivatives and the like can be used with the proviso that they are capable of raising substantially the same immune response as the native protein.

Preferred proteins of the invention are those pneumococcal proteins which are exposed on the outer surface of the pneumococcus (capable of being recognised by a host's immune system during at least part of the life cycle of the pneumococcus), or are proteins which are secreted or released by the pneumococcus. Most preferably, the protein is a toxin, adhesin, 2-component signal tranducer, or lipoprotein of *Streptococcus pneumoniae*, or immunologically functional equivalents thereof.

Particularly preferred proteins to be included in such a combination vaccine, include but are not limited to: pneumolysin (preferably detoxified by chemical treatment or mutation) [Mitchell et al. Nucleic Acids Res. 1990 Jul. 11; 18(13): 4010 "Comparison of pneumolysin genes and proteins from *Streptococcus pneumoniae* types 1 and 2.", Mitchell et al. Biochim Biophys Acta 1989 Jan. 23; 1007(1): 67-72 "Expression of the pneumolysin gene in *Escherichia coli*: rapid purification and biological properties.", WO 96/05859 (A. Cyanamid), WO 90/06951 (Paton et al), WO 99/03884 (NAVA)]; PspA and transmembrane deletion variants thereof (U.S. Pat. No. 5,804,193—Briles et al.); PspC and transmembrane deletion variants thereof (WO 97/09994—Briles et al); PsaA and transmembrane deletion variants thereof (Berry & Paton, Infect Immun 1996 December; 64(12):5255-62 "Sequence heterogeneity of PsaA, a 37-kilodalton putative adhesin essential for virulence of *Streptococcus pneumoniae*"); pneumococcal choline binding proteins and transmembrane deletion variants thereof; CbpA and transmembrane deletion variants thereof (WO 97/41151; WO 99/51266); Glyceraldehyde-3-phosphate—dehydrogenase (Infect. Immun. 1996 64:3544); HSP70 (WO 96/40928); PcpA (Sanchez-Beato et al. FEMS Microbiol Lett 1998, 164:207-14); M like protein, SB patent application No. EP 0837130; and adhesin 18627, SB Patent application No. EP 0834568.

The proteins used in the present invention are preferably selected from the group pneumolysin, PsaA, PspA, PspC, CbpA or a combination of two or more such proteins. The present invention also encompasses immunologically functional equivalents of such proteins (as defined above).

Within the composition, the protein can help to induce a T-cell mediated response against pneumococcal disease—particularly required for protection against pneumonia—which cooperates with the humoral branch of the immune system to inhibit invasion by pneumococci, and to stimulate opsonophagocytosis.

Further advantages of including the protein antigen is presentation of further antigens for the opsonophagocytosis process, and the inhibition of bacterial adhesion (if an adhesin is used) or the neutralisation of toxin (if a toxin is used).

Accordingly in an embodiment of the invention there is provided a *Streptococcus pneumoniae* vaccine comprising a pneumococcus polysaccharide conjugate vaccine comprising polysaccharide antigens derived from at least four serotypes, preferably at least seven serotypes, more preferably at least eleven serotypes, and at least one, but preferably two, *Streptococcus pneumoniae* proteins. Preferably one of the proteins is Pneumolysin or PsaA or PspA or CbpA (most preferably detoxified pneumolysin). A preferred combination contains at least pneumolysin or a derivative thereof and PspA.

As mentioned above, a problem associated with the polysaccharide approach to vaccination, is the fact that polysaccharides per se are poor immunogens. To overcome this, polysaccharides may be conjugated to protein carriers, which provide bystander T-cell help. It is preferred, therefore, that the polysaccharides utilised in the invention are linked to such a protein carrier. Examples of such carriers which are currently commonly used for the production of polysaccharide immunogens include the Diphtheria and Tetanus toxoids (DT, DT CRM197 and TT respectively), Keyhole Limpet Haemocyanin (KLH), OMPC from *N. meningitidis*, and the purified protein derivative of Tuberculin (PPD).

A number of problems are, however, associated with each of these commonly used carriers (see section "Problems Associated with Commonly-Used Carriers" above).

The present invention provides in a preferred embodiment a new carrier for use in the preparation of polysaccharide-based immunogen constructs, that does not suffer from these disadvantages. The preferred carrier for the pneumococcal polysaccharide based immunogenic compositions (or vaccines) is protein D from *Haemophilus influenzae* (EP 594610-B), or fragments thereof. Fragments suitable for use include fragments encompassing T-helper epitopes. In particular a protein D fragment will preferably contain the N-terminal ⅓ of the protein.

A further preferred carrier for the pneumococcal polysaccharide is the pneumococcal protein itself (as defined above in section "Pneumococcal Proteins of the invention").

The vaccines of the present invention are preferably adjuvanted. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes.

It is preferred that the adjuvant be selected to be a preferential inducer of a TH1 type of response to aid the cell mediated branch of the immune response.

TH1 Adjuvants of the Invention

High levels of Th1-type cytokines tend to favour the induction of cell mediated immune responses to a given antigen, whilst high levels of Th2-type cytokines tend to favour the induction of humoral immune responses to the antigen. It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include, Monophosphoryl lipid A or a derivative thereof, particularly 3-de-O-acylated monophosphoryl lipid A, and a combination of monophosphoryl lipid A, preferably 3-de-O-acylated monophosphoryl lipid A (3D-MPL) together with an aluminium salt.

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21, 3D-MPL and tocopherol in an oil in water emulsion is described in WO 95/17210, and is a preferred formulation.

Preferably the vaccine additionally comprises a saponin, more preferably QS21. The formulation may also comprises an oil in water emulsion and tocopherol (WO 95/17210).

The present invention also provides a method for producing a vaccine formulation comprising mixing a protein of the present invention together with a pharmaceutically acceptable excipient, such as 3D-MPL.

Unmethylated CpG containing oligonucleotides (WO 96/02555) are also preferential inducers of a TH1 response and are suitable for use in the present invention.

Particularly preferred compositions of the invention comprise one or more conjugated pneumococcal polysaccharides, one or more pneumococcal proteins and a Th1 adjuvant. The induction of a cell mediated response by way of a pneumococcal protein (as described above) and the cooperation between both arms of the immuen system may be aided using such a Th-1 adjuvant, resulting in a particularly effective vaccine against pneumococcal disease in general, and, importantly, against pneumococcal pneumonia in the elderly.

In a further aspect of the present invention there is provided an immunogen or vaccine as herein described for use in medicine.

In a still further aspect of the invention, a composition is provided comprising a pneumococcal polysaccharide conjugate and a Th1 adjuvant (preferably 3D-MPL) which is capable of seroconverting or inducing a humoral antibody response against the polysaccharide antigen within a population of non-responders.

10-30% of the population are known to be non-responders to polysaccharide immunization (do not respond to more than 50% of serotypes in a vaccine) (Konradsen et al., Scand. J. Immun 40:251 (1994); Rodriguez et al., JID, 173:1347 (1996)). This can also be the case for conjugated vaccines (Musher et al. Clin. Inf. Dis. 27:1487 (1998)). This can be particularly serious for high risk areas of the population (infants, toddlers and the elderly).

The present inventors have found that a combination of a conjugated pneumococcal polysaccharide (which is prone to low response in a particular population) with a Th1 adjuvant (see "Th1 adjuvants of the invention" above) can surprisingly overcome this non-responsiveness. Preferably 3D-MPL should be used, and most preferably 3D-MPL devoid of aluminium-based adjuvant (which provides a better response still). The present invention thus provides such compositions, and further provides a method of treating non-responders to pneumococcal polysaccharides by administering such compositions, and still further provides a use of a Th1 adjuvant in the manufacture of a medicament comprising conjugated pneumococcal polysaccharide antigens, in the treatment against (or protection from) pneumococcal disease in individuals which are non-responsive to the polysaccharide antigen.

In one embodiment there is a method of preventing or ameliorating pneumonia in an elderly human comprising administering a safe and effective amount of a vaccine, as described herein, comprising a *Streptoccocus pneumoniae* polysaccharide antigen and either a Th1 adjuvant, or a pneumococcal protein (and preferably both), to said elderly patient.

In a further embodiment there is provided a method of preventing or ameliorating otitis media in Infants or toddlers, comprising administering a safe and effective amount of a vaccine comprising a *Streptococcus pneumoniae* polysaccharide antigen and either a *Streptococcus pneumoniae* protein antigen or a Th1 adjuvant (and preferably both), to said Infant or toddler.

Preferably in the methods of the invention as described above the polysaccharide antigen is present as a polysaccharide protein conjugate.

Vaccine Preparations of the Invention

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage).

The amount of conjugate antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 0.1-100 µg of polysaccharide, preferably 0.1-50 µg, preferably 0.1-10 µg, of which 1 to 5 µg is the most preferable range.

The content of protein antigens in the vaccine will typically be in the range 1-100 µg, preferably 5-50 µg, most typically in the range 5-25 µg.

Optimal amounts of components for a particular vaccine can be ascertained by standard studies involving observation of appropriate immune responses in subjects. Following an initial vaccination, subjects may receive one or several booster immunisations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

B) Selected Pneumococcal Polysaccharide Conjugate+3D-MPL Compositions

For the purposes of this invention, the term "pneumococcal polysaccharide conjugates of the invention" describes those conjugates of *Streptococcus pneumoniae* capsular polysaccharides which are more immunogenic in compositions comprising 3D-MPL in comparison with compositions comprising 3D-MPL in conjunction with an aluminium-based adjuvant (for example, conjugates of serotype 4; serotype 6B; serotype 18C; serotype 19F; or serotype 23F).

For the purposes of this invention, the term "substantially devoid of aluminium-based adjuvants" describes a composition which does not contain sufficient aluminium-based adjuvant (for example aluminium hydroxide, and, particularly, aluminium phosphate) to cause any decrease in the immunogenicity of a pneumococcal polysaccharide conjugate of the invention in comparison to an equivalent composition comprising 3D-MPL with no added aluminium-based adjuvant. Preferably the antigenic composition should contain adjuvant that consists essentially of 3D-MPL. Quantities of aluminium-based adjuvant added per dose should preferably be less than 50 µg, more preferably less than 30 µg, still more preferably less than 10 µg, and most preferably there is no aluminium-based adjuvant added to the antigenic compositions of the invention.

For the purposes of this invention, the determination of whether a pneumococcal polysaccharide conjugate is significantly more immunogenic in compositions comprising 3D-MPL in comparison with compositions comprising 3D-MPL in conjunction with an aluminium-based adjuvant, this should be established as described in Example 2. As an indication of whether a composition is significantly more immunogenic when comprising 3D-MPL alone, the ratio of GMC IgG concentration (as determined in Example 2) between compositions comprising 3D-MPL alone versus an equivalent composition comprising 3D-MPL in conjunction with aluminium phosphate adjuvant should be more than 2, preferably more than 5, more preferably more than 7, still more preferably more than 9, and most preferably more than 14.

Amongst the problems associated with the polysaccharide approach to vaccination, is the fact that polysaccharides per se are poor immunogens. Strategies, which have been designed to overcome this lack of immunogenicity, include the linking (conjugating) of the polysaccharide to large protein carriers, which provide bystander T-cell help. It is preferred that the pneumococcal polysaccharides of the invention are linked to a protein carrier which provides bystander T cell help. Examples of such carriers which may be used include the Diphtheria, Diphtheria mutant, and Tetanus toxoids (DT, CRM197 and TT respectively), Keyhole Limpet Haemocyanin (KLH), the purified protein derivative of Tuberculin (PPD), and OMPC of *Neisseria meningitidis*.

Most preferably, protein D from *Haemophilus influenzae* (EP 0 594 610-B), or fragments thereof (see section C), is used as the immunogenic protein carrier for the pneumococcal polysaccharides of the invention.

In one embodiment the antigenic composition of the invention comprises pneumococcal polysaccharide serotype (PS) 4 conjugated to an immunogenic protein and formulated with 3D-MPL adjuvant, where the composition is substantially devoid of aluminium-based adjuvant. In further embodiments, the antigenic composition comprises PS 6B, 18C, 19F, or 23F, respectively, conjugated to an immunogenic protein and formulated with 3D-MPL adjuvant, where the composition is substantially devoid of aluminium-based adjuvant.

In a still further embodiment of the invention, a combination antigenic composition is provided comprising two or more pneumococcal polysaccharide conjugates from the group PS 4, PS 6B, PS 18C, PS19F, and PS 23F formulated with 3D-MPL adjuvant, where the composition is substantially devoid of aluminium-based adjuvant.

The immunogenicity of pneumococcal polysaccharide conjugates of the invention is not significantly effected by combination with other pneumococcal polysaccharide conjugates (Example 3). Accordingly, a preferred aspect of the invention provides a combination antigenic composition comprising one or more pneumococcal polysaccharide conjugates of the invention in combination with one or more further pneumococcal polysaccharide conjugates, where the composition is formulated with 3D-MPL adjuvant, but is substantially devoid of aluminium-based adjuvant.

In further preferred embodiments of the invention, combination antigenic compositions are provided which contain at least one and preferably 2, 3, 4 or all 5 of the PS 4, 6B, 18C, 19F, or 23F pneumococcal polysaccharide conjugates, and in addition any combination of other pneumococcal polysaccharide conjugates, which are formulated with 3D-MPL adjuvant but substantially devoid of aluminium-based adjuvant.

Typically the *Streptococcus pneumoniae* combination antigenic composition of the present invention will comprise polysaccharide conjugate antigens, wherein the polysaccharides are derived from at least four, seven, eleven, thirteen, fifteen or twenty-three serotypes (see "*Streptococcus pneumoniae* Polysaccharide Antigens of the Invention" above for preferred combinations of serotypes depending on the disease to be treated).

The antigenic compositions of the invention are preferably used as vaccine compositions to prevent (or treat) pneumococcal infections, particularly in the elderly and infants and toddlers.

Further embodiments of the present invention include: the provision of the above antigenic compositions for use in medicine; a method of inducing an immune response to a *Streptococcus pneumoniae* capsular polysaccharide conjugate, comprising the steps of administering a safe and effective amount of one of the above antigenic compositions to a patient; and the use of one of the above antigenic compositions in the manufacture of a medicament for the prevention (or treatment) of pneumococcal disease.

For the prevention/amelioration of pneumonia in the elderly (+55 years) population and Otitis media in Infants (up to 18 months) and toddlers (typically 18 months to 5 years), it is a further preferred embodiment of the invention to combine a multivalent *Streptococcus pneumonia* polysaccharide conjugate formulated as herein described with a *Streptococcus pneumoniae* protein or immunologically functional equivalent thereof. See above section "Pneumococcal Proteins of the invention" for preferred proteins/protein combinations.

Preferably the antigenic compositions (and vaccines) hereinbefore described are lyophilised up until they are about to be used, at which point they are extemporaneously reconstituted with diluent. More preferably they are lyophilsed in the presence of 3D-MPL, and are extemporaneously reconstituted with saline solution.

Lyophilising the compositions results in a more stable composition (for instance it prevents the breakdown of the polysaccharide antigens). The process is also surprisingly responsible for a higher antibody titre still against the pneumococcal polysaccharides. This has been shown to be particularly significant for PS 6B conjugates. Another aspect of the invention is thus a lyophilised antigenic composition comprising a PS 6B conjugate adjuvanted with 3D-MPL and substantially devoid of aluminium-based adjuvants.

For preparation of the vaccines, see above "Vaccine Preparations of the Invention" section.

C) Bacterial Polysaccharide—Protein D Conjugates

The trend towards combination vaccines has the advantage of reducing discomfort to the recipient, facilitating scheduling, and ensuring completion of regiment; but there is also the concomitant risk of reducing the vaccine's efficacy (see above for discussion on epitope suppression through overuse of carrier proteins). It would be, therefore, advantageous to make vaccine combinations which meet the needs of a population, and which, in addition, do not exhibit immunogenic interference between their components. These advantages may be realised by the immunogenic compositions (or vaccines) of the invention, which are of particular benefit for administration of combination vaccines to high risk groups such infants, toddlers or the elderly.

The present invention provides a protein D from *Haemophilus influenzae*, or fragments thereof, as a carrier for polysaccharide based immunogenic composition, including vaccines. Fragments suitable for use include fragments encompassing T-helper epitopes. In particular protein D fragment will preferably contain the N-terminal ⅓ of the protein.

Protein D is an IgD—binding protein from *Haemophilus influenzae* (EP 0 594 610 B1) and is a potential immunogen.

Polysaccharides to be conjugated to Protein D contemplated by the present invention include, but are not limited to the Vi polysaccharide antigen against *Salmonella typhi*, meningococcal polysaccharides (including type A, C, W135 and Y, and the polysaccharide and modified polysaccharides of group B meningococcus), polysaccharides from *Staphylococcus aureus*, polysaccharides from *Streptococcus agalactae*, polysaccharides from *Streptococcus pneumoniae*, polysaccharides from *Mycobacterium* e.g. *Mycobacterium tuberculosis* (such as mannophosphoinisitides trehaloses, mycolic acid, mannose capped arabinomannans, the capsule therefrom and arabinogalactans), polysaccharide from *Cryptococcus neoformans*, the lipopolysaccharides of non-typeable *Haemophilus influenzae*, the capsular polysaccharide from *Haemophilus influenzae* b, the lipopolysaccharides of *Moraxella catharralis*, the lipopolysaccharides of *Shigella sonnei*, the lipopeptidophosphoglycan (LPPG) of *Trypanosoma cruzi*, the cancer associated gangliosides GD3, GD2, the tumor associated mucins, especially the T-F antigen, and the sialyl T-F antigen, and the HIV associated polysaccharide that is structurally related to the T-F antigen.

The polysaccharide may be linked to the carrier protein by any known method (for example, by Likhite, U.S. Pat. No. 4,372,945 and by Armor et al., U.S. Pat. No. 4,474,757). Preferably, CDAP conjugation is carried out (WO 95/08348).

In CDAP, the cyanylating reagent 1-cyano-dimethylaminopyridinium tetrafluoroborate (CDAP) is preferably used for the synthesis of polysaccharide-protein conjugates. The cyanilation reaction can be performed under relatively mild conditions, which avoids hydrolysis of the alkaline sensitive polysaccharides. This synthesis allows direct coupling to a carrier protein.

The polysaccharide is solubilized in water or a saline solution. CDAP is dissolved in acetonitrile and added immediately to the polysaccharide solution. The CDAP reacts with the hydroxyl groups of the polysaccharide to form a cyanate ester. After the activation step, the carrier protein is added. Amino groups of lysine react with the activated polysaccharide to form an isourea covalent link.

After the coupling reaction, a large excess of glycine is then added to quench residual activated functions. The product is then passed through a gel permeation to remove unreacted carrier protein and residual reagents. Accordingly the invention provides a method of producing polysaccharide protein D conjugates comprising the steps of activating the polysaccharide and linking the polysaccharide to the protein D.

In a preferred embodiment of the invention there is provided an immunogenic composition (or vaccine) formulation for the prevention of *Streptococcus pneumoniae* infections.

The mechanisms by which pneumococci spread to the lung, the cerebrospinal fluid and the blood is poorly understood. Growth of bacteria reaching normal lung alveoli is inhibited by their relative dryness and by the phagocytic activity of alveolar macrophages. Any anatomic or physiological changes of these co-ordinated defenses tend to augment the susceptibility of the lungs to infection. The cell-wall of *Streptococcus pneumoniae* has an important role in generating an inflammatory response in the alveoli of the lung (Gillespie et al. (1997), I&I 65: 3936).

Typically the *Streptococcus pneumoniae* vaccine of the present invention will comprise protein D polysaccharide conjugates, wherein the polysaccharide is derived from at least four, seven, eleven, thirteen, fifteen or 23 serotypes. See above "*Streptococcus pneumoniae* Polysaccharide Antigens of the Invention" for preferred combinations of serotypes depending on the disease to be treated.

In a further embodiment of the invention there is provided a *Neisseria meningitidis* vaccine; in particular from serotypes A, B, C W-135 and Y. *Neisseria meningitidis* is one of the most important causes of bacterial meningitis. The carbohydrate capsule of these organisms can act as a virulence determinant and a target for protective antibody. Carbohydrates are nevertheless well known to be poor immunogens in young children. The present invention provides a particularly suitable protein carrier for these polysaccharides, protein D, which provides T-cell epitopes that can activate a T-cell response to aid polysaccharide antigen specific B-cell proliferation and maturation, as well as the induction of an immunological memory.

In an alternative embodiment of the invention there is provided a capsular polysaccharide of *Haemophilus influenzae* b (PRP)—protein D conjugate.

The present invention also contemplates combination vaccines which provide protection against a range of different pathogens. A protein D carrier is surprisingly useful as a carrier in combination vaccines where multiple polysaccharide antigens are conjugated. As mentioned above, epitope suppression is likely to occur if the same carrier is used for each polysaccharide. WO 98/51339 presented compositions to try to minimise this interference by conjugating a proportion of the polysaccharides in the composition onto DT and the rest onto TT.

Surprisingly, the present inventors have found protein D is particularly suitable for minimising such epitopic suppression effects in combination vaccines. One or more polysaccharides in a combination may be advantageously conjugated onto protein D, and preferably all antigens are conjugated onto protein D within such combination vaccines.

A preferred combination includes a vaccine that affords protection against *Neisseria meningitidis* C and Y (and preferably A) infection wherein the polysaccharide antigen from one or more of serotypes Y and C (and most preferably A) are linked to protein D.

*Haemophilus influenzae* polysaccharide based vaccine (PRP conjugated with preferably TT, DT or CRM197, or most preferably with protein D) may be formulated with the above combination vaccines.

Many Paediatric vaccines are now given as a combination vaccine so as to reduce the number of injections a child has to receive. Thus for Paediatric vaccines other antigens may be formulated with the vaccines of the invention. For example the vaccines of the invention can be formulated with, or administered separately, but at the same time with the well known 'trivalent' combination vaccine comprising Diphtheria toxoid (DT), tetanus toxoid (TT), and pertussis components [typically detoxified Pertussis toxoid (PT) and filamentous haemagglutinin (FHA) with optional pertactin (PRN) and/or agglutinin 1+2], for example the marketed vaccine INFANRIX-DTPa™ (SmithKlineBeecham Biologicals) which contains DT, TT, PT, FHA and PRN antigens, or with a whole cell pertussis component for example as marketed by SmithKlineBeecham Biologicals s.a., as TRITANRIX™.

The combined vaccine may also comprise other antigen, such as Hepatitis B surface antigen (HBsAg), Polio virus antigens (for instance inactivated trivalent polio virus—IPV), *Moraxella catarrhalis* outer membrane proteins, non-typeable *Haemophilus influenzae* proteins, *N. meningitidis* B outer membrane proteins.

Examples of preferred *Moraxella catarrhalis* protein antigens which can be included in a combination vaccine (especially for the prevention of otitis media) are: OMP106 [WO 97/41731 (Antex) & WO 96/34960 (PMC)]; OMP21; LbpA & LbpB [WO 98/55606 (PMC)]; TbpA & TbpB [WO 97/13785 & WO 97/32980 (PMC)]; CopB [Helminen M E, et al. (1993) Infect. Immun 61:2003-2010]; UspA1/2 [WO 93/03761 (University of Texas)]; and OmpCD. Examples of non-typeable *Haemophilus influenzae* antigens which can be included in a combination vaccine (especially for the prevention of otitis media) include: Fimbrin protein [(U.S. Pat. No. 5,766,608—Ohio State Research Foundation)] and fusions comprising peptides therefrom [eg LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and TbpB; Hia; Hmw-1,2; Hap; and D15.

Preferred Peadiatric vaccines contemplated by the present invention are:
a) *N. meningitidis* C polysaccharide conjugate and *Haemophilus influenzae* b polysaccharide conjugate, optionally with *N. meningitidis* A and/or Y polysaccharide conjugate, provided that at least one polysaccharide antigen, and preferably all are conjugated to protein D.
b) Vaccine a) with, DT, TT, pertussis components (preferable PT, FHA and PRN), Hepatitis B surface antigen and IPV (inactivated trivalent poliovirus vaccine).
c) *Streptococcus pneumoniae* polysaccharide antigens conjugated to protein D.
d) Vaccine c) with one or more antigens from *Moraxella catarrhalis* and/or non-typeable *Haemophilus influenzae*.

All the above combination vaccines, can benefit from the inclusion of protein D as a carrier. Clearly, the more carriers that are involved in a combination vaccine (for instance to overcome epitope suppression), the more expensive and complex the final vaccine. Having all, or the majority, of the polysaccharide antigens of a combination vaccine conjugated to protein D thus provides a considerable advantage For the prevention of pneumonia in the elderly (+55 years) population and Otitis media in Infants or toddlers, it is a preferred embodiment of the invention to combine a multivalent *streptococcus pneumonia* polysaccharide—protein D antigens as herein described with a *Streptococcus pneumoniae* protein or immunologically functional equivalent thereof. See above section "Pneumococcal Proteins of the invention" for preferred proteins/protein combinations that can be included in such a combination.

Accordingly the present invention provides an immunogenic composition comprising a *Streptococcus pneumoniae* polysaccharide—protein D conjugate and a *Streptococcus pneumoniae* protein antigen.

The polysaccharide—protein D conjugate antigens of the present invention are preferably adjuvanted in the vaccine formulation of the invention. Suitable adjuvants include an aluminium salt such as aluminum hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes.

For elderly vaccines it is preferred that the adjuvant be selected to be a preferential inducer of a TH1 type of response.

For particular Th1 adjuvants see "Th1 adjuvants of the invention" above.

In a further aspect of the present invention there is provided an immunogen or vaccine as herein described for use in medicine.

For vaccine preparation/administration of the conjugate, see "Vaccine Preparation of the Invention" above.

Protein D is also advantageously used in a vaccine against otitis media, as it is in itself an immunogen capable of producing B-cell mediated protection against non-typeable *H. influenzae* (ntHi). ntHi may invade host cells, and evade the B-cell mediated effects induced by the protein antigen. The present inventors have surprisingly found a way of increasing the effectiveness of protein D (either by itself or as a carrier for a polysaccharide) as an antigen for an otitis media vaccine. This is done by adjuvanting the protein D such that a strong Th1 response is induced in the subject such that the cell mediated arm of the immune system is optimised against protein D. This is surprisingly achieved using a lyophilised composition comprising protein D and a Th1 adjuvant (preferably 3D-MPL) which is reconstituted shortly before administration. The invention thus also provides such compositions, a process for making such compositions (by lyophilising a mixture comprising protein D and a Th1 adjuvant), and a use of such a composition in the treatment of otitis media.

In a broader sense, the inventors envisage that lyophilising an immunogen in the presence of a Th1 adjuvant (see "Th1 adjuvants of the invention"), preferably 3D-MPL, will generally augment the Th1 immune response against the immunogen. The present invention is therefore applicable to any immunogen to which a stronger Th1 immune response is required. Such immunogens comprise bacterial, viral and tumour protein antigens, as well as self proteins and peptides.

EXAMPLES

The examples illustrate, but do not limit the invention.

Example 1

*S. pneumoniae* Capsular Polysaccharide

The 11-valent candidate vaccine includes the capsular polysaccharides serotypes 1, 3, 4, 5, 6B, 7F, 9V, 14, 18C, 19F and 23F which were made essentially as described in EP 72513. Each polysaccharide is activated and derivatised using CDAP chemistry (WO 95/08348) and conjugated to the protein carrier. All the polysaccharides are conjugated in their native form, except for the serotype 3 (which was size-reduced to decrease its viscosity).

Protein Carrier:

The protein carrier selected is the recombinant protein D (PD) from Non typeable *Haemophilus influenzae*, expressed in *E. coli*.

Expression of Protein D

*Haemophilus influenzae* Protein D

Genetic Construction for Protein D Expression

Starting Materials

The Protein D Encoding DNA

Protein D is highly conserved among *H. influenzae* of all serotypes and non-typeable strains. The vector pHIC348 containing the DNA sequence encoding the entire protein D gene has been obtained from Dr. A. Forsgren, Department of Medical Microbiology, University of Lund, Malmö General Hospital, Malmö, Sweden. The DNA sequence of protein D has been published by Janson et al. (1991) Infect. Immun. 59: 119-125.

The Expression Vector pMG1

The expression vector pMG1 is a derivative of pBR322 (Gross et al., 1985) in which bacteriophage λ derived control elements for transcription and translation of foreign inserted genes were introduced (Shatzman et al., 1983). In addition, the Ampicillin resistance gene was exchanged with the Kanamycin resistance gene.

The *E. coli* Strain AR58

The *E. coli* strain AR58 was generated by transduction of N99 with a P1 phage stock previously grown on an SA500 derivative (galE::TN10, lambdaKil⁻ cI857 ΔH1). N99 and SA500 are *E. coli* K12 strains derived from Dr. Martin Rosenberg's laboratory at the National Institute of Health.

The Expression Vector pMG 1

For the production of protein D, the DNA encoding the protein has been cloned into the expression vector pMG 1. This plasmid utilises signals from lambdaphage DNA to drive the transcription and translation of inserted foreign genes. The vector contains the promoter PL, operator OL and two utilisation sites (NutL and NutR) to relieve transcriptional polarity effects when N protein is provided (Gross et al., 1985). Vectors containing the PL promoter, are introduced into an *E. coli* lysogenic host to stabilise the plasmid DNA. Lysogenic host strains contain replication-defective lambdaphage DNA integrated into the genome (Shatzman et al., 1983). The chromosomal lambdaphage DNA directs the synthesis of the cI repressor protein which binds to the OL repressor of the vector and prevents binding of RNA polymerase to the PL promoter and thereby transcription of the inserted gene. The cI gene of the expression strain AR58 contains a temperature sensitive mutant so that PL directed transcription can be regulated by temperature shift, i.e. an increase in culture temperature inactivates the repressor and synthesis of the foreign protein is initiated. This expression system allows controlled synthesis of foreign proteins especially of those that may be toxic to the cell (Shimataka & Rosenberg, 1981).

The *E. coli* Strain AR58

The AR58 lysogenic *E. coli* strain used for the production of the protein D carrier is a derivative of the standard NIH *E. coli* K12 strain N99 (F⁻ su⁻ galK2, lacZ⁻ thr⁻). It contains a defective lysogenic lambdaphage (galE::TN10, lambdaKil⁻ cI857 ΔH1). The Kil⁻ phenotype prevents the shut off of host macromolecular synthesis. The cI857 mutation confers a temperature sensitive lesion to the cI repressor. The ΔH1 deletion removes the lambdaphage right operon and the hosts bio, uvr3, and chlA loci. The AR58 strain was generated by transduction of N99 with a P1 phage stock previously grown on an SA500 derivative (galE::TN10, lambdaKil⁻ cI857 ΔH1). The introduction of the defective lysogen into N99 was selected with tetracycline by virtue of the presence of a TN10 transposon coding for tetracyclin resistance in the adjacent galE gene.

Construction of Vector pMGMDPPrD

The pMG 1 vector which contains the gene encoding the non-structural S1 protein of Influenzae virus (pMGNSI) was used to construct pMGMDPPrD. The protein D gene was amplified by PCR from the pHIC348 vector (Janson et al. 1991) with PCR primers containing NcoI and XbaI restriction sites at the 5' and 3' ends, respectively. The NcoI/XbaI fragment was then introduced into pMGNS1 between NcoI and XbaI thus creating a fusion protein containing the N-terminal 81 amino acids of the NS1 protein followed by the PD protein. This vector was labeled pMGNS1PrD.

Based on the construct described above the final construct for protein D expression was generated. A BamHI/BamHI fragment was removed from pMGNS1PrD. This DNA hydrolysis removes the NS1 coding region, except for the first three N-terminal residues. Upon religation of the vector a gene encoding a fusion protein with the following N-terminal amino acid sequence has been generated:

```
-----MDP SSHSSNMANT-----    (SEQ ID NO: 1)
NS1              Protein D
```

The protein D does not contain a leader peptide or the N-terminal cysteine to which lipid chains are normally attached. The protein is therefore neither excreted into the periplasm nor lipidated and remains in the cytoplasm in a soluble form.

The final construct pMG-MDPPrD was introduced into the AR58 host strain by heat shock at 37° C. Plasmid containing bacteria were selected in the presence of Kanamycin. Presence of the protein D encoding DNA insert was demonstrated by digestion of isolated plasmid DNA with selected endonucleases. The recombinant E. coli strain is referred to as ECD4.

Expression of protein D is under the control of the lambda $P_L$ promoter/$O_L$ Operator. The host strain AR58 contains a temperature-sensitive cI gene in the genome which blocks expression from lambda $P_L$ at low temperature by binding to $O_L$. Once the temperature is elevated cI is released from $O_L$ and protein D is expressed. At the end of the fermentation the cells are concentrated and frozen.

The extraction from harvested cells and the purification of protein D was performed as follows. The frozen cell culture pellet is thawed and resuspended in a cell disruption solution (Citrate buffer pH 6.0) to a final $OD_{650}$=60. The suspension is passed twice through a high pressure homogenizer at P=1000 bar. The cell culture homogenate is clarified by centrifugation and cell debris are removed by filtration. In the first purification step the filtered lysate is applied to a cation exchange chromatography column (SP SEPHAROSE® Fast Flow). PD binds to the gel matrix by ionic interaction and is eluted by a step increase of the ionic strength of the elution buffer.

In a second purification step impurities are retained on an anionic exchange matrix (Q SEPHAROSE® Fast Flow). PD does not bind onto the gel and can be collected in the flow through.

In both column chromatography steps fraction collection is monitored by OD. The flow through of the anionic exchange column chromatography containing the purified protein D is concentrated by ultrafiltration.

The protein D containing ultrafiltration retentate is finally passed through a 0.2 µm membrane.

Chemistry:
Activation and Coupling Chemistry:

The activation and coupling conditions are specific for each polysaccharide. These are given in Table 1. Native polysaccharide (except for PS3) was dissolved in NaCl 2M or in water for injection. The optimal polysaccharide concentration was evaluated for all the serotypes.

From a 100 mg/ml stock solution in acetonitrile, CDAP (CDAP/PS ratio 0.75 mg/mg PS) was added to the polysaccharide solution. 1.5 minute later, 0.2M triethylamine was added to obtain the specific activation pH. The activation of the polysaccharide was performed at this pH during 2 minutes at 25° C. Protein D (the quantity depends on the initial PS/PD ratio) was added to the activated polysaccharide and the coupling reaction was performed at the specific pH for 1 hour. The reaction was then quenched with glycine for 30 minutes at 25° C. and overnight at 4° C.

The conjugates were purified by gel filtration using a SEPHACRYL® 500HR gel filtration column equilibrated with 0.2M NaCl.

The carbohydrate and protein content of the eluted fractions was determined. The conjugates were pooled and sterile filtered on a 0.22 µm sterilizing membrane. The PS/Protein ratios in the conjugate preparations were determined Characterisation:

Each conjugate was characterised and met the specifications described in Table 2. The polysaccharide content (µg/ml) was measured by the Resorcinol test and the protein content (µg/ml) by the Lowry test. The final PS/PD ratio (w/w) is determined by the ratio of the concentrations.

Residual DMAP Content (ng/µg PS):

The activation of the polysaccharide with CDAP introduces a cyanate group in the polysaccharide and DMAP (4-dimethylamino-pyridin) is liberated. The residual DMAP content was determined by a specific assay developed at SB.

Free Polysaccharide Content (%):

The free polysaccharide content of conjugates kept at 4° C. or stored 7 days at 37° C. was determined on the supernatant obtained after incubation with α-PD antibodies and saturated ammonium sulfate, followed by a centrifugation.

An α-PS/α-PS ELISA was used for the quantification of free polysaccharide in the supernatant. The absence of conjugate was also controlled by an α-PD/α-PS ELISA. Reducing the quantity of free polysaccharide results in an improved conjugate vaccine.

Antigenicity:

The antigenicity on the same conjugates was analyzed in a sandwich-type ELISA wherein the capture and the detection of antibodies were α-PS and α-PD respectively.

Free Protein Content (%):

The level of "free" residual protein D was determined by using a method with SDS treatment of the sample. The conjugate was heated 10 min at 100° C. in presence of SDS 0.1% and injected on a SEC-HPLC gel filtration column (TSK 3000-PWXL). As protein D is dimer, there is a risk of over-estimating the level of "free" protein D by dissociation the structure with SDS.

Molecular Size ($K_{av}$):

The molecular size was performed on a SEC-HPLC gel filtration column (TSK 5000-PWXL).

Stability:

The stability was measured on a HPLC-SEC gel filtration (TSK 6000-PWXL) for conjugates kept at 4° C. and stored for 7 days at 37° C.

The 11-valent characterization is given in Table 2

The protein conjugates can be adsorbed onto aluminium phosphate and pooled to form the final vaccine.

Conclusion:

Immunogenic conjugates have been produced, that have since been shown to be components of a promising vaccine. The optimised CDAP conditions for the best quality final conjugated pneumococcal polysaccharide product was discovered for each of the 11 valencies. Conjugates of these pneumococcal polysaccharides obtainable by the above improved (optimised) CDAP process (regardless of the carrier protein, but preferably protein D) is thus a further aspect of the invention.

Example 2

Study of the Effect of Advanced Adjuvants on the Immunogenicity of the 11-Valent Pneumococcal PS-PD Conjugate Vaccine in Infant Rats Infant rats were immunised with 11 valent pneumococcal PS-PD conjugate vaccine at a dosage of 0.1 µg each polysaccharide (made according to the method of Example 1), and using the following adjuvant formulations: none, $AlPO_4$, 3D-MPL, 3D-MPL on $AlPO_4$.

The formulation with only 3D-MPL was statistically (and surprisingly) more immunogenic (greatest GMC IgG) than for the other formulations for 5 out of 11 antigens. This was true both at high and low concentrations of 3D-MPL.

Opsonophagocytosis confirmed the GMC results.

Materials and Methods

Immunisation Protocol

Infant OFA rats were randomised to different mothers and were 7 days old when they received the first immunisation. They received 2 additional immunisations 14 and 28 days later. A bleed was performed on day 56 (28 days post III). All vaccines were injected s.c., and there were 10 rats per vaccine group.

The rats were immunised with an 11 valent pneumococcal conjugate vaccine comprising the following polysaccharide serotypes conjugated onto protein D: 1, 3, 4, 5, 6B, 7F, 9V, 14, 18C, 19F, 23F.

Formulation

To examine the effect of different advanced adjuvants, the dosage of conjugate was held constant at 0.1 µg of each polysaccharide, and the adjuvants $AlPO_4$ and 3D-MPL were formulated in different dosages and combinations, including no adjuvant at all. These are listed numerically in Table 3 for reference.

Adsorption on $AlPO_4$

The concentrated, adsorbed monovalents were prepared according to the following procedure. 50 µg $AlPO_4$ (pH 5.1) was mixed with 5 µg conjugated polysaccharides for 2 hours. The pH was adjusted to pH 5.1 and the mixture was left for a further 16 hours. 1500 mM NaCl was added to make up the salt concentration to 150 mM. After 5 minutes 5 mg/mL 2-phenoxyethanol was added. After a further 30 minutes the pH was adjusted to 6.1, and left for more than 3 days at 4° C.

Preparation of Diluents

Three diluents were prepared in NaCl 150 mM/5 mg/mL phenoxyethanol

---

A: $AlPO_4$ at 1 mg/ml.
B: 3D-MPL on $AlPO_4$ at 250 and 1000 µg/ml respectively
Weight ratio 3D-MPL/$AlPO_4$ = 5/20
C: 3D-MPL on $AlPO_4$ at 561 and 1000 µg/ml respectively
Weight ratio 3D-MPL/$AlPO_4$ = 50/89

---

Preparation of Adsorbed Undecavalent

The eleven concentrated, adsorbed PS-PD monovalents were mixed at the correct ratio. The complement of $AlPO_4$ was added as the diluent A. When required, 3D-MPL was added either as an aqueous solution (non adsorbed, Way 1 see below) or as the diluent B or C (3D-MPL adsorbed on $AlPO_4$ at 2 doses, Way 2, see below).

Way 1

3D-MPL was added to the combined adsorbed conjugates as an aqueous suspension. It was mixed to the undecavalent for 10 minutes at room temperature and stored at 4° C. until administration.

Way 2

3D-MPL was preabsorbed onto $AlPO_4$ before addition to the combined adsorbed conjugates (diluent B and C). To prepare 1 ml of diluent, an aqueous suspension of 3D-MPL (250 or 561 µg) was mixed with 1 mg of $AlPO_4$ in NaCl 150 mM pH 6.3 for 5 min at room temperature. This solution was diluted in NaCl pH 6.1/phenoxy and incubated overnight at 4° C.

Preparation of Non-Adsorbed Undecavalent

The eleven PS-PD conjugates were mixed and diluted at the right ratio in NaCl 150 mM pH 6.1, phenoxy. When required, 3D-MPL was added as a solution (non adsorbed).

The formulations for all injections were prepared 18 days before the first administration.

ELISA

The ELISA was performed to measure rat IgG using the protocol derived from the WHO Workshop on the ELISA procedure for the quantitation of IgG antibody against *Streptococcus pneumoniae* capsular polysaccharides in human serum. In essence, purified capsular polysaccharide is coated directly on the microtitre plate. Serum samples are pre-incubated with the cell-wall polysaccharide common to all pneumococcus (substance C) and which is present in ca. 0.5% in pneumococcal polysaccharides purified according to disclosure (EP 72513 B1). Jackson ImmunoLaboratories Inc. reagents were employed to detect bound murine IgG. The titration curves were referenced to internal standards (monoclonal antibodies) modeled by logistic log equation. The calculations were performed using SoftMax Pro software. The maximum absolute error on these results expected to be within a factor of 2. The relative error is less than 30%.

Opsonophagocytosis

Opsonic titres were determined for serotypes 3, 6B, 7F, 14, 19F and 23F using the CDC protocol (*Streptococcus pneumoniae* Opsonophagocytosis using Differentiated HL60 cells, version 1.1) with purified human PMN and baby rabbit complement. Modification included the use of in-house pneumococcal strains, and the phagocytic HL60 cells were replaced by purified human neutrophils PMN (there is a high degree of correlation between these phagocytic cells). In addition, 3 mm glass beads were added to the microtitre wells to increase mixing, and this allowed reduction of the phagocyte:bacteria ratio which was recommended to be 400.

Results

IgG Concentrations

The geometric mean IgG concentrations determined for every serotype, and PD are shown in Tables 4 to 10. For serotypes 6B, 14, 19F and 23F, previous results obtained using a tetravalent formulation are included for comparison.

The highest IgG concentrations have been highlighted in Tables 4 to 10. The statistical p value for 3D-MPL compositions vs. 3D-MPL/$AlPO_4$ compositions is in Table 11. Adjuvant formulation number 4 (non-adsorbed conjugates with high dose 3D-MPL) that gives the highest GMC's for 9 out of 11 cases. In 5/11 cases, MPL at the low dose is the second most immunogenic. In addition, adjuvantation gives higher GMC's than by modifying the dose for all serotypes (data not shown), and this is statistically significant for serotypes 4, 6B, 7F, 18C and 23F ($p<0.05$ from 95% CI).

Opsonophagocytosis

Opsonophagocytosis results on pooled sera is shown for serotypes 3, 6B, 7F, 14, 19F and 23F in Tables 4 to 8. For the most part, these opsonic titres confirm the GMC IgG. Indeed, the correlation with IgG concentration is greater than 85% for serotypes 6B, 19F, 23F (data not shown). For serotype 3, it is important to note that only the 3D-MPL group induced opsonic activity above the threshold.

Conclusions

In this experiment, it was unexpected that the use of 3D-MPL alone would induce the highest IgG concentrations.

The maximal GMC IgG obtained with modifying the adjuvant was compared with the maximal GMC obtained by modifying the PS dosage, and it was found that 3D-MPL could induce significantly higher responses in 5/11 serotypes.

Table 11 shows that when 3D-MPL and 3D-MPL/AlPO$_4$ compositions are compared (comparing the process of formulation, and the dose of 3D-MPL), 5 of the polysaccharide conjugates are significantly improved, in terms of immunogenicity, when formulated with just 3D-MPL rather than 3D-MPL plus AlPO$_4$: PS 4, PS 6B, PS 18C, PS 19F, and PS 23F.

Example 3

Study of the Effect of Combination on the Immunogenicity of PS 4, PS 6B, PS 18C, PS19F, and PS 23F Conjugates in Adult Rats Adult rats were immunised with pneumococcal polysaccharide-protein D conjugate vaccines either individually, or combined in a multivalent composition (either tetra-, penta-, hepta-, or decavalent). Groups of 10 rats were immunised twice days apart, and test bleeds were obtained on day 28 and day 42 (14 days after the $2^{nd}$ dose).

The sera were tested by ELISA for IgG antibodies to the pneumococcal polysaccharides. All conjugates induced specific IgG antibodies as measured by ELISA. Table 12 shows the effect of combination of monovalent PS 6B, PS 18C, PS 19F, and PS 23F protein D conjugates on their immunogenicity in adult rats, as measured by IgG concentration at 14 days post $2^{nd}$ dose.

Statistical analysis was performed on all samples to determine if differences in antibody concentration upon combination were significant. The combination of any of serotypes PS 6B, PS 18C, PS 19F, and PS 23F protein D conjugates in a multivalent vaccine did not significantly change their immunogenicity.

TABLE 1

Specific activation/coupling/quenching conditions of PS *S. pneumoniae*-Protein D conjugates

| | Serotype | | | | | |
| --- | --- | --- | --- | --- | --- | --- |
| | 1 | 3 (μfluid.) | 4 | 5 | 6B | 7F |
| PS conc.(mg/ml) | 2.0 | 3.0 | 2.0 | 7.5 | 5.4 | 3.0 |
| PS dissolution | NaCl 2M | NaCl 2M | H$_2$O | H$_2$O | NaCl 2M | NaCl 2M |
| PD conc.(mg/ml) | 5.0 | 5.0 | 5.0 | 5.0 | 5.0 | 5.0 |
| Initial PS/PD Ratio (w/w) | 1/1 | 1/1 | 1/1 | 1/1 | 1/1 | 1/1 |
| CDAP conc. (mg/mg PS) | 0.75 | 0.75 | 0.75 | 0.75 | 0.75 | 0.75 |
| pH$_a$ = pH$_c$ = pH$_q$ | 9.0/9.0/9.0 | 9.0/9.0/9.0 | 9.0/9.0/9.0 | 9.0/9.0/9.0 | 9.5/9.5/9.0 | 9.0/9.0/9.0 |

| | Serotype | | | | |
| --- | --- | --- | --- | --- | --- |
| | 9V | 14 | 18C | 19F | 23F |
| PS conc.(mg/ml) | 2.5 | 2.5 | 2.0 | 4.0 | 3.3 |
| PS dissolution | NaCl 2M | NaCl 2M | H$_2$O | NaCl 2M | NaCl 2M |
| PD conc.(mg/ml) | 5.0 | 5.0 | 5.0 | 5.0 | 5.0 |
| Initial PS/PD Ratio (w/w) | 1/0.75 | 1/0.75 | 1/1 | 1/0.5 | 1/1 |
| CDAP conc. (mg/mg PS) | 0.75 | 0.75 | 0.75 | 0.75 | 0.75 |
| pH$_a$ = pH$_c$ = pH$_q$ | 8.5/8.5/9.0 | 9.0/9.0/9.0 | 9.0/9.0/9.0 | 10/9.5/9.0 | 9.0/9.0/9.0 |

TABLE 2

Specifications of the 11 valent pneumococcoal PS-PD vaccine (first numbers of the batch code indicates serotype)

| Criteria | D01PDJ227 | D03PDJ236 | D4PDJ228 | D5PDJ235 | D6PDJ209 |
| --- | --- | --- | --- | --- | --- |
| Ratio PS/Prot (w/w) | 1/0.66 | 1/1.09 | 1/0.86 | 1/0.86 | 1/0.69 |
| Free polysac. content (%) <10% | 1 | 1 | 7 | 9 | 0 |
| Free protein content (%) <15% | 8 | <1 | 19 | 21 | 9 |
| DMAP content (ng/μg PS) <0.5 ng/μg PS | 0.2 | 0.6 | 0.4 | 1.2 | 0.3 |

TABLE 2-continued

Specifications of the 11 valent pneumococcoal PS-PD vaccine
(first numbers of the batch code indicates serotype)

| Molecular size ($K_{av}$) | 0.18 | 0.13 | 0.12 | 0.11 | 0.13 |
|---|---|---|---|---|---|
| Stability | no shift | no shift | no shift | low shift | no shift |

|  | D07PDJ225 | D09PDJ222 | D14PDJ202 | D18PDJ221 | D19PDJ206 | D23PDJ212 |
|---|---|---|---|---|---|---|
| Ratio PS/Prot (w/w) | 1/0.58 | 1/0.80 | 1/0.68 | 1/0.62 | 1/0.45 | 1/0.74 |
| Free polysac. content (%) <10% | 1 | <1 | <1 | 4 | 4 | 0 |
| Free protein content (%) <15% | 8 | 0.3 | 3 | 21 | 10 | 12 |
| DMAP content (ng/µg PS) <0.5 ng/µg PS | 0.1 | 0.6 | 0.3 | 0.2 | 0.1 | 0.9 |
| Molecular size ($K_{av}$) | 0.14 | 0.14 | 0.17 | 0.10 | 0.12 | 0.12 |
| Stability | no shift | no shift | no shift | no shift | shift | no shift |

TABLE 3

Summary Table of Adjuvant Formulations tested with
11-Valent Pneumococcal PS-PD in Infant Rats

| Group | AlPO4 | MPL | Method | Description |
|---|---|---|---|---|
| 1 |  |  |  | None |
| 2 | 100 |  |  | AlPO4 |
| 3 |  | 5 |  | MPL low |
| 4 |  | 50 |  | MPL High |
| 5 | 100 | 5 | Way 1 | Way 1 low |
| 6 | 100 | 50 | Way 1 | Way 1 high |
| 7 | 100 | 5 | Way 2 | Way 2 low |
| 8 | 100 | 50 | Way 2 | Way 2 high |

TABLE 4

Serotype 6B Geometric Mean IgG Concentration, Seroconversion, and Mean Opsonic
Titre on Day 28 Post III Immunisation of Infant Rats with 11-Valent PS-PD
using Different Adjuvants (And Comparison with Tetravalent Immunisation)

| Group | AlPO4 µg | MPL µg | Method | 6B GMC IgG (µg/ml) Tetravalent | 6B Seroconversion Tetravalent | 6B Opso Titre* Tetravalent | 6B GMC IgG (µg/ml) Undecavalent | 6B Seroconversion Undecavalent | 6B Opso Titre* Undecavalent |
|---|---|---|---|---|---|---|---|---|---|
| 1 |  |  |  | 0.047 | 2/10 | 12.5 | 0.004 | 1/10 | <6.25 |
| 2 | 100 |  |  | 0.048 | 4/10 | 65 | 0.019 | 4/10 | <6.25 |
| 3 |  | 5 |  |  |  |  | 1.345 | 10/10 | 43 |
| 4 |  | 50 |  |  |  |  | 4.927 | 10/10 | 192 |
| 5 | 100 | 5 | 1 |  |  |  | 0.042 | 7/10 | <6.25 |
| 6 | 100 | 50 | 1 |  |  |  | 0.255 | 10/10 | <6.25 |
| 7 | 100 | 5 | 2 | 0.033 | 3/10 | <6.25 | 0.048 | 8/10 | <6.25 |
| 8 | 100 | 50 | 2 |  |  |  | 0.057 | 8/10 | <6.25 |

TABLE 5

Serotype 14 Geometric Mean IgG Concentration, Seroconversion, and Mean Opsonic
Titre on Day 28 Post III Immunisation of Infant Rats with 11-Valent PS-PD
using Different Adjuvants (And Comparison with Tetravalent Immunisation)

| Group | AlPO4 | MPL | Method | 14 GMC IgG (µg/ml) Tetravalent | 14 Serconversion Tetravalent | 14 Opsonic Titre* Tetravalent | 14 GMC IgG (µg/ml) Undecavalent | 14 Serconversion Undecavalent | 14 Opsonic Titre* Undecavalent |
|---|---|---|---|---|---|---|---|---|---|
| 1 |  |  |  | 0.046 | 3/10 | 64 | 0.022 | 3/10 | <6.25 |
| 2 | 100 |  |  | 0.99 | 10/10 | 88 | 0.237 | 8/10 | 27 |
| 3 |  | 5 |  |  |  |  | 0.233 | 10/10 | 41 |
| 4 |  | 50 |  |  |  |  | 0.676 | 10/10 | 81 |
| 5 | 100 | 5 | 1 |  |  |  | 0.460 | 9/10 | 67 |
| 6 | 100 | 50 | 1 |  |  |  | 0.477 | 10/10 | 98 |
| 7 | 100 | 5 | 2 | 0.81 | 10/10 | 49 | 0.165 | 8/10 | 81 |
| 8 | 100 | 50 | 2 |  |  |  | 1.611 | 10/10 | 133 |

TABLE 6

Serotype 19F Geometric Mean IgG Concentration, Seroconversion, and Mean Opsonic Titre on Day 28 Post III Immunisation of Infant Rats with 11-Valent PS-PD using Different Adjuvants (And Comparison with Tetravalent Immunisation)

| Group | AlPO4 µg | MPL µg | Method | 19F GMC IgG (µg/ml) Tetravalent | 19F Seroconversion Tetravalent | 19F Opsonic Titre* Tetravalent | 19F GMC IgG (µg/ml) Undecavalent | 19F Seroconversion Undecavalent | 19F Opsonic Titre* Undecavalent |
|---|---|---|---|---|---|---|---|---|---|
| 1 |  |  |  | 0.04 | 2/10 | 64 | 0.021 | 2/10 | <6.25 |
| 2 | 100 |  |  | 1.07 | 9/10 | 367 | 0.222 | 7/10 | 79 |
| 3 |  | 5 |  |  |  |  | 4.028 | 10/10 | 296 |
| 4 |  | 50 |  |  |  |  | 21.411 | 10/10 | 1276 |
| 5 | 100 | 5 | 1 |  |  |  | 1.649 | 10/10 | 172 |
| 6 | 100 | 50 | 1 |  |  |  | 2.818 | 10/10 | 208 |
| 7 | 100 | 5 | 2 | 1.09 | 10/10 | 193 | 0.766 | 10/10 | 323 |
| 8 | 100 | 50 | 2 |  |  |  | 3.539 | 10/10 | 241 |

TABLE 7

Serotype 23F Geometric Mean IgG Concentration, Seroconversion, and Mean Opsonic Titre on Day 28 Post III Immunisation of Infant Rats with 11-Valent PS-PD using Different Adjuvants (And Comparison with Tetravalent Immunisation)

| Group | AlPO4 µg | MPL µg | Method | 23F GMC IgG (µg/ml) Tetravalent | 23F Seroconversion Tetravalent | 23F Opsonic Titre* Tetravalent | 23F GMC IgG (µg/ml) Undecavalent | 23F Seroconversion Undecavalent | 23F Opsonic Titre* Undecavalent |
|---|---|---|---|---|---|---|---|---|---|
| 1 |  |  |  | 0.06 | 2/10 | <6.25 | 0.152 | 3/10 | <6.25 |
| 2 | 100 |  |  | 0.29 | 10/10 | 70 | 0.56 | 8/10 | <6.25 |
| 3 |  | 5 |  |  |  |  | 2.296 | 9/10 | 389 |
| 4 |  | 50 |  |  |  |  | 4.969 | 10/10 | >1600 |
| 5 | 100 | 5 | 1 |  |  |  | 0.462 | 5/10 | 17 |
| 6 | 100 | 50 | 1 |  |  |  | 0.635 | 8/10 | 54 |
| 7 | 100 | 5 | 2 | 0.38 | 10/10 | <6.25 | 0.203 | 3/10 | 18 |
| 8 | 100 | 50 | 2 |  |  |  | 0.501 | 7/10 | 43 |

TABLE 8

Serotypes 3 and 7F Geometric Mean IgG Concentration, Seroconversion, and Mean Opsonic Titre on Day 28 Post III Immunisation of Infant Rats with 11-Valent PS-PD using Different Adjuvants

| Group | AlPO4 µg | MPL µg | Method | 3 GMC IgG (µg/ml) | 3 Seroconversion | 3 Opsonic Titre* | 7F GMC IgG (µg/ml) | 7F Seroconversion | 7F Opsonic Titre* |
|---|---|---|---|---|---|---|---|---|---|
| 1 |  |  |  | 0.003 | 1/10 | <6.25 | 0.040 | 7/10 | <6.25 |
| 2 | 100 |  |  | 0.008 | 6/10 | <6.25 | 0.25 | 9/10 | 43 |
| 3 |  | 5 |  | 0.070 | 10/10 | <6.25 | 2.435 | 10/10 | 477 |
| 4 |  | 50 |  | 0.108 | 10/10 | 18 | 2.569 | 10/10 | 332 |
| 5 | 100 | 5 | 1 | 0.015 | 10/10 | <6.25 | 0.579 | 10/10 | 54 |
| 6 | 100 | 50 | 1 | 0.027 | 10/10 | <6.25 | 0.611 | 9/10 | 59 |
| 7 | 100 | 5 | 2 | 0.006 | 10/10 | <6.25 | 0.154 | 8/10 | 30 |
| 8 | 100 | 50 | 2 | 0.034 | 10/10 | <6.25 | 0.638 | 9/10 | 140 |

TABLE 9

Serotypes 1, 4 and 5 Geometric Mean IgG Concentration and Seroconversion on Day 28 Post III Immunisation of Infant Rats with 11-Valent PS-PD using Different Adjuvants

| Group | AlPO4 µg | MPL µg | Method | 1 GMC IgG (µg/ml) | 1 Seroconversion | 4 GMC IgG (µg/ml) | 4 Seroconversion | 5 GMC IgG (µg/ml) | 5 Seroconversion |
|---|---|---|---|---|---|---|---|---|---|
| 1 |  |  |  | 0.026 | 4/10 | 0.005 | 0/10 | 0.040 | 3/10 |
| 2 | 100 |  |  | 0.282 | 8/10 | 0.052 | 5/10 | 0.774 | 9/10 |
| 3 |  | 5 |  | 1.614 | 10/10 | 3.452 | 10/10 | 7.927 | 10/10 |
| 4 |  | 50 |  | 2.261 | 10/10 | 7.102 | 10/10 | 13.974 | 10/10 |
| 5 | 100 | 5 | 1 | 0.568 | 10/10 | 0.676 | 10/10 | 3.015 | 10/10 |
| 6 | 100 | 50 | 1 | 1.430 | 10/10 | 0.419 | 9/10 | 5.755 | 10/10 |
| 7 | 100 | 5 | 2 | 0.478 | 10/10 | 0.267 | 9/10 | 2.062 | 10/10 |
| 8 | 100 | 50 | 2 | 1.458 | 10/10 | 0.423 | 10/10 | 5.009 | 10/10 |

TABLE 10

Serotypes 9V, 18C and PD Geometric Mean IgG Concentration and Seroconversion on Day 28
Post III Immunisation of Infant Rats with 11-Valent PS-PD using Different Adjuvants

| Group | AlPO4 µg | MPL µg | Method | 9V GMC IgG (µg/ml) | 9V Seroconversion | 18C GMC IgG (µg/ml) | 18C Seroconversion | PD GMC IgG (µg/ml) | PD Seroconversion |
|---|---|---|---|---|---|---|---|---|---|
| 1 | | | | 0.018 | 0/10 | 0.013 | 1/10 | 0.003 | 0/10 |
| 2 | 100 | | | 0.489 | 6/10 | 0.092 | 5/10 | 0.993 | 10/10 |
| 3 | | 5 | | 0.482 | 7/10 | 6.560 | 10/10 | 3.349 | 10/10 |
| 4 | | 50 | | 11.421 | 10/10 | 14.023 | 10/10 | 5.446 | 10/10 |
| 5 | 100 | 5 | 1 | 2.133 | 9/10 | 0.690 | 10/10 | 11.407 | 10/10 |
| 6 | 100 | 50 | 1 | 2.558 | 10/10 | 1.771 | 10/10 | 1.258 | 10/10 |
| 7 | 100 | 5 | 2 | 1.536 | 10/10 | 0.528 | 10/10 | 1.665 | 8/10 |
| 8 | 100 | 50 | 2 | 2.448 | 9/10 | 0.980 | 10/10 | 5.665 | 10/10 |

TABLE 11

The statistical significance (p value) of whether certain pneumococcal polysaccharide conjugates had improved immunogenicity when formulated with 3D-MPL alone versus with 3D-MPL/AlPO4.

| serotype | 50 µg 3D-MPL v 3D-MPL/AlPO$_4$ Way 1 | Way 2 | 5 µg 3D-MPL vs 3D-MPL/AlPO$_4$ Way 1 | Way 2 |
|---|---|---|---|---|
| 1 | 0.3 | 0.05 | 0.079 | 0.11 |
| 3 | 0.075 | 0.01 | 0.27 | 0.008 |
| 4 | 0.002 | 0.0003 | 0.02 | 0.003 |
| 5 | 0.04 | 0.002 | 0.1 | 0.12 |
| 6B | 0.001 | 0.0001 | 0.001 | 0.0006 |
| 7F | 0.13 | 0.15 | 0.01 | 0.005 |
| 9V | 0.02 | 0.02 | 0.1 | 0.04 |
| 14 | 0.65 | 0.21 | 0.3 | 0.66 |
| 18C | 0.0008 | 0.0002 | 0.006 | 0.004 |
| 19F | 0.0009 | 0.006 | 0.21 | 0.04 |
| 23F | 0.002 | 0.0004 | 0.01 | 0.0004 |

A p value under 0.01 is considered highly significant. Way 1 and Way 2 indicate the method of formulation.

TABLE 12

Geometric Mean IgG concentration (µg/mL) on day 14 post 2$^{nd}$ dose after immunisation of adult rats with 1.0 µg polysaccharide-protein D conjugate alone or combined in tetravalent, pentavalent, heptavalent or decavalent vaccine.

| Vaccines | Serotypes | | | | |
|---|---|---|---|---|---|
| | 4 H | 6B T | 18C H | 19F T | 23F T |
| Alone | 9.3 | 0.11 | 15 | 5.2 | 2.5 |
| Combined | 4 | 0.23 | 3.7 | 3.7 | 2.8 |

These data are combined from 5 separate experiments.
T: combined in tetravalent (T) (PS 6B, 14, 19F, 23F), pentavalent (T plus PS 3), heptavalent (H) (T plus PS 4, 9V and 18C), and decavalent (H plus PS 1, 5 and 7F) combination vaccines.
H: combined in heptavalent (H) (T plus PS 4, 9V and 18C), and decavalent (H plus PS 1, 5 and 7F) combination vaccines.

Example 4

Beneficial Impact of the Addition of Pneumolysin and 3D-MPL on the Protective Effectiveness of PD-Conjugated 11-Valent Polysaccharide Vaccine Against Pneumococcal Lung Colonization in Mice Immunological Read-Outs
ELISA Dosage of Pneumolysin-Specific Serum IgG Maxisorp Nunc immunoplates were coated for 2 hours at 37° C. with 100 µl/well of 2 µg/ml recombinant native pneumolysin (PLY) diluted in PBS. Plates were washed 3 times with NaCl 0.9% TWEEN® 20 0.05% buffer. Then, serial 2-fold dilutions (in PBS/TWEEN® 20 0.05%, 100 µl per well) of an anti-PLY serum reference added as a standard curve (starting at 670 ng/ml IgG) and serum samples (starting at 1/10 dilution) were incubated for 30 minutes at 20° C. under agitation. After washing as previously described, peroxydase-conjugated goat anti-mouse IgG (Jackson) diluted 5000× in PBS/TWEEN® 20 0.05% were incubated (100 µl/well) for 30 minutes at 20° C. under agitation. After washing, plates were incubated for 15 min at room temperature with 100 µl/well of revelation buffer (OPDA 0.4 mg/ml and $H_2O_2$ 0.05% in 100 mM pH 4.5 citrate buffer). Revelation was stopped by adding 50 µl/well HCl 1N. Optical densities were read at 490 and 620 nm by using EMAX® immunoreader (Molecular Devices). Antibody titre were calculated by the 4 parameter mathematical method using SoftMaxPro software.

Hemolysis Inhibition

This assay was done for measuring the ability of serum antibodies to inhibit the pneumolysin (PLY) hemolytic activity. In order to eliminate the cholesterol (susceptible of interacting with PLY), serum samples were treated 2× as follows: they were mixed with 1 equal volume of chloroform and then incubated for 45 minutes under agitation. Supernatants were collected after centrifugation for 10 minutes at 1000 rpm. Cholesterol-cleared sera were diluted (serial 2-fold dilutions in 1 mM dithiothreitol, 0.01% BSA, 15 mM TRIS, 150 mM NaCl, pH 7.5) in 96 well microplates (Nunc). Fifty µl of a solution containing 4 HU (Hemolysis Unit) of PLY were added in each well and incubated for 15 minutes at 37° C. Then, 100 µl of sheep red blood cells (1% solution) were added for 30 minutes at 37° C. After centrifugation for 10 minutes at 1000 rpm, supernatants (150 µl) were collected and put into another 96-well microplate for optical density reading at 405 nm. Results were expressed as mid-point dilution titers.

Pneumolysin Chemical Detoxification

Recombinant native pneumolysin (PLY) was dialyzed against Phosphate 50 mM NaCl 500 mM pH 7.6 buffer. All following steps were done at 39.5° C. under episodic agitation. At day 1, TWEEN® 80 10% (1/250 v/v), N-acetyl tryptophan 57.4 mM pH 7.6 (3/100 v/v), glycin 2.2 M in Phosphate buffer (1/100 v/v) and formaldehyde 10% in Phosphate buffer (3/100 v/v) were added into PLY solution. At days 2 and 3, formaldehyde 10% was added again, at 3/100 and 2/100 v/v/ratio, respectively. Incubation at 39.5° C. was sustained until day 7 under episodic agitation. Finally, PLY was dialyzed against Phosphate 50 mM NaCl 500 mM pH 7.6 buffer. Complete inactivation of PLY was demonstrated in the hemolysis assay.

Pneumococcal Intranasal Challenge in OF1 mice

Seven week-old OF1 female mice were intranasally inoculated under anesthesia with $5.10^5$ CFU of mouse-adapted *S. pneumoniae* serotype 6B. Lungs were removed at 6 hours after challenge and homogenized (Ultramax, 24000 rpm, 4° C.) in Todd Hewith Broth (THB, Gibco) medium. Serial 10-fold dilutions of lung homogenates were plated overnight at 37° C. onto Petri dishes containing yeast extract-supplemented THB agar. Pneumococcal lung infection was determined as the number of CFU/mouse, expressed as logarithmic weighted-average. Detection limit was 2.14 log CFU/mouse.

Example 4A

3D-MPL Adjuvant Effect on Anti-Pneumolysin Immune Response

In the present example, we evaluated the impact of 3D-MPL adjuvantation on the immune response to native recombinant pneumolysin (PLY, provided by J. Paton, Children's Hospital, North Adelaide, Australia) and its chemically detoxified counterpart (DPLY). Chemical detoxification was done as described above.

Figure 1B:
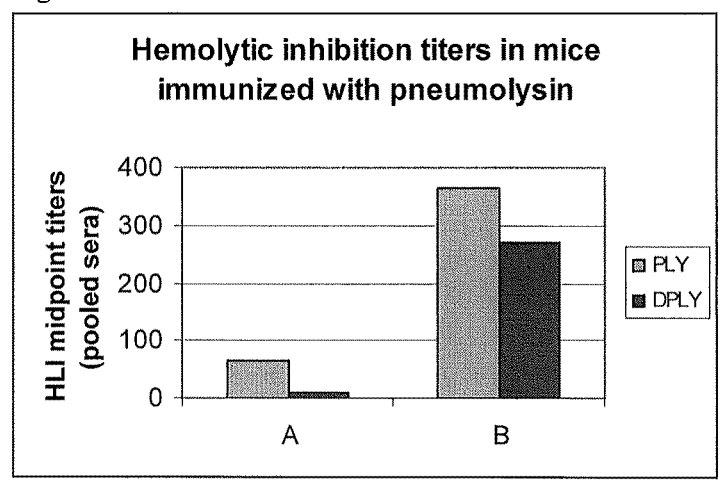
FIG. 1B: Hemolytic inhibition titers in mice immunized with pneumolysin.

Groups of 10 female 6 week-old Balb/c mice were intramuscularly immunized at days 0, 14 and 21 with 1 ng PLY or DPLY contained in either A: AlPO4 100 ng; or B: AlPO4 100 μg+5 μg 3D-MPL (3 de-O-acylated monophosphoryl lipid A, supplied by Ribi Immunochem). FIGS. 1A and 1B show ELISA IgG and HemoLysis Inhibition titers (HLI) measured in post-III sera.

Whichever the antigen, best immune responses were induced in animals vaccinated with 3D-MPL-supplemented formulations. Interestingly, DPLY was as immunogenic as PLY when administered with AlPO4+3D-MPL, while being a weaker immunogen in AlPO4 formulation. This showed the advantageous ability of 3D-MPL to improve the antibody response to detoxified pneumolysin.

In compositions containing pneumolysin, it may be preferable to use chemically detoxified pneumolysin rather than mutationally detoxified pneumolysin. This is because detoxified mutants obtained to date still have residual toxin activity—chemically detoxified pneumolysin does not. It is therefore considered another aspect of the invention that, in general, compositions comprising pneumolysin (or pneumolysin mutants) that has been chemically detoxified for use in a vaccine, should be adjuvanted with a Th1 adjuvant, preferably 3D-MPL. Such compositions are provided by the invention. A method of increasing the immune response of chemically-detoxified pneumolysin within an immunogenic composition comprising the steps of adding a Th1 adjuvant (preferably 3D-MPL) to the composition, is also envisaged.

Example 4B

Beneficial Impact of the Addition of an Attenuated Mutant of Pneumolysis and 3D-MPL Adjuvant on the Protective Effectiveness of PD-Conjugated 11-Valent Polysaccharide Vaccine Against Pneumococcal Lung Colonization in OF1 Mice Intranasally Challenged with Serotype 6B In the present example, we evaluated the prophylactic efficacy of a vaccine containing the 11-valent polysaccharide-protein D conjugate, attenuated mutant pneumolysin antigen (PdB, WO 90/06951) and AlPO4+3D-MPL adjuvants, compared to the classical AlPO4-adsorbed 11-valent polysaccharide-protein D conjugate formulation.

Groups of 12 female 4 week-old OF1 mice were immunized subcutaneously at days 0 and 14 with formulations containing A: 50 μg AlPO4; B: 0.1 μg PS/serotype of PD-conjugated 11-valent polysaccharide vaccine+50 μg AlPO4; or C, 0.1 μg PS/serotype of PD-conjugated 11-valent polysaccharide vaccine+10 μg PdB (provided by J. Paton, Children's Hospital, North Adelaide, Australia)+50 μg AlPO4+5 μg 3D-MPL (supplied by Ribi Immunochem). Challenge was done at day 21 as described above.

Figure 1C:
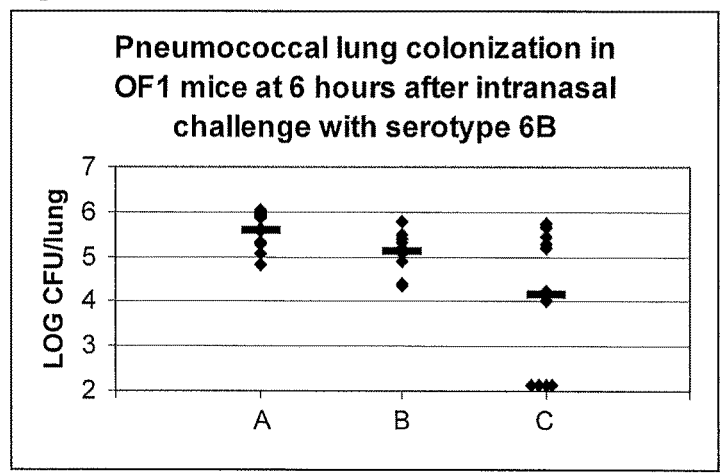
FIG. 1C: Pneumococcal lung colonization in OF1 mice at 6 hours after intranasal challenge with serotype 6B.

As shown in FIG. 1C, a very significant protection ($p<0.007$) was conferred by the 11-valent polysaccharide conjugate vaccine supplemented with PdB and adjuvanted with AlPO4+MPL (black bars represent the arithmetic mean). On the contrary, no significant protection was observed in animals immunized with the 11-valent polysaccharide conjugate/AlPO4 formulation. This result proved that the addition of pneumolysin antigen (even attenuated) and 3D-MPL adjuvant enhanced the effectiveness of the 11-valent polysaccharide conjugate vaccine against pneumonia.

Example 4C

Immune Correlates of the Protection Showed in Example 4B

In order to establish the immune correlates of protection conferred in example 4B, by the 11-valent polysaccharide conjugate vaccine supplemented with attenuated mutant pneumolysin (PdB) and 3D-MPL, pre-challenge serological antibody responses to polysaccharide 6B and PdB were measured as described above.

Antibody titers were then compared to bacteria colony numbers measured in lungs of the corresponding animals collected at 6 hours post-challenge. $R^2$ were calculated on Log/Log linear regressions.

Calculated $R^2$ were equal to 0.18 and 0.02 for anti-PdD and anti-6B antibody responses, respectively. This showed the absence of correlation between humoral immune responses and protection for both antigens. Anti-6B antibody titers were not significantly different in the groups immunized with the 11-valent conjugate vaccine (GMT=0.318 ng/ml) or with the same vaccine supplemented with PdD and 3D-MPL (GMT=0.458 ng/ml). Therefore, the protection improvement seen with formulation C was not solely due to a higher antibody response to polysaccharide 6B.

Taken together, the results suggest that protection was not mediated by humoral immune responses alone, but rather also by a cell-mediated immunity induced by the PdB antigen in the presence of 3D-MPL. This gave additional support to the addition of protein antigen(s) and potent adjuvant(s) in the pneumococcal polysaccharide conjugate vaccine, so as to coordinate both arms of the immune system for optimal protection.

Example 5

The Cooperation of Both Arms of the Immune System in Mice Actively Immunised with Pneumolysin and Passively Immunised with Antibodies Against Pneumococcal PS Example 5A Find the Concentration of Passively Administered Anti-6B-Polysaccharide (Anti-PS) Antibody Protecting Against Pneumonia Method Vaccine Groups: Four groups of 16 mice were passively immunised (i.p.) on day −1 with 100 μl of undiluted rat anti-polysaccharide antisera according to the groups detailed below. (total 64 mice)

| Group | Specificity | IgG Concentration in Antisera |
|---|---|---|
| G1 | α-PS -6B | 5 μg/ml. |
| G2 | α-PS -6B | 2 μg/ml. |
| G3 | α-PS -6B | 0.75 μg/ml. |
| G4 | Control | 0 μg/ml. |

Animals: 64 male CD-1 mice from Charles River, Canada, weighing approx 35 g (approx 10 weeks old).

Anesthesia: Mice were anesthetized with isoflurane (3%) plus $O_2$(1 L/min).

Organism: S. pneumoniae N1387 (serotype 6) was harvested from trypticase soy agar plates (TSA) supplemented with 5% horse blood and suspended in 6 ml of PBS. Immediately prior to infection, 1 ml bacterial suspension was diluted into 9 ml of cooled molten nutrient agar (BBL) and kept at 41° C. Mice received approx 6.0 log10 cfu/mouse in a volume 50 ul.

Infection: On day 0 mice were anesthetized as described above and infected with S. pneumoniae N1387 (50 μl cooled bacterial suspension) by intra-bronchial instillation via non-surgical intra-tracheal intubation. This method was described by Woodnut and Berry (Antimicrob. Ag. Chemotherap. 43: 29 (1999)).

Samples: On day 3 post infection, 8 mice/group were sacrificed by CO2 overdose and lungs were excised and homogenized in 1 ml PBS. Tenfold serial dilutions were prepared in PBS to enumerate viable bacterial numbers. Samples were inoculated (20 μl) in triplicate onto TSA plates supplemented with 5% horse blood and incubated overnight at 37° C. prior to evaluation. Further sets of mice were sacrificed on day 7 and sampled as above.

Results:

| IgG conc (ug/ml) in rat sera | Bacterial numbers (log 10 cfu/lungs) at days post infection | |
|---|---|---|
| | 3 | 8 |
| 5 | 6.7 ± 0.7 (1/7) | 7.2 ± 0.7 (5/8) |
| 2 | 6.5 ± 0.7 (1/7) | 6.9 ± 1.8 (4/7) |
| 0.75 | 7.7 ± 0.5 (5/8) | 4.8 ± 1.4 (2/8) |
| 0 | 6.7 ± 1.5 (3/6) | 6.3 ± 1.5 (3/9) |

Figures in parenthesis are numbers of animals that died prior to sample time.

Conclusion: In general, there was no significant difference in bacterial numbers isolated from any of the treatment groups. This indicates that no measurable protection was afforded by the anti-polysaccharide at concentrations up to and including 5 μg/ml.

This is similar to what is observed in some human clinical trials, that is, anti-polysaccharide body is insufficient to protect against pneumococcal pneumonia in some populations.

Example 5B

Determine the Protection from Pneumonia Afforded by Active Administration of Ply (Pneumolysin) with or without Adjuvant, and Synergy with Sub-Optimal Anti-PS Antibody Method Animals: 128 male CD-1 mice (6 weeks old at old at immunisation, 10 weeks old at infection) from Charles River, St. Constant, Quebec, Canada Animals weighed approx 20 gm at 6 weeks and 38 g at 10 weeks.

Immunisations: Six groups of 16 mice were immunised by subcutaneous injection on days −22 and −14 with 100 ul of vaccine as detailed below. (Total 128 mice). PdB (WO 90/06951) was obtained courtesy of Dr. James Paton, Australia. 3D-MPL was obtained from Ribi/Corixa.

On day −1, specific groups (see Table below) were immunised (i.p. 100 μl) passively with a concentration of 4.26 μg/ml (4 ml of 5 μg/ml+1.3 ml of 2 μg/ml) mouse anti-polysaccharide antibody.

| Group | Injection Volume Active | Vaccine given days −22, −14 (Dosage μg) | Injection Volume Passive | Passive IgG (day −1) |
|---|---|---|---|---|
| 1-1 | 100 μl s.c. | PdB/AlPO4 (10/50) | | None |
| 1-2 | 100 μl s.c. | PdB/MPL/AlPO4 (10/5/50) | | None |
| 1-3 | 100 μl s.c. | PdB/AlPO4 (10/50) | 100 μl i.p. | α-PS |
| 1-4 | 100 μl s.c. | PdB/MPL/AlPO4 (10/5/50) | 100 μl i.p. | α-PS |
| 1-5 | 100 μl s.c. | MPL/AlPO4 (5/50) | 100 μl i.p. | α-PS |
| 1-6 | 100 μl s.c. | MPL/AlPO4 (5/50) | | None |

Infection: On day 0, mice were anesthetized (3% isoflurane plus 1 L/min $O_2$). Bacterial inocula were prepared by harvesting growth of S. pneumoniae N1387 (serotype 6) from trypticase soy agar plates (TSA) supplemented with 5% horse blood and suspending in 6 ml of PBS. A ten-fold dilution (1 ml plus 9 ml) was prepared in cooled molten nutrient agar (kept at 41° C.) immediately prior to infection. Mice were infected by intra-bronchial instillation via intra-tracheal intubation and received approximately 6.0 log10 cfu/mouse in a volume of 50 μl. This method was described by Woodnut and Berry (Antimicrob. Ag. Chemotherap. 43: 29 (1999)).

Samples: At 72 post infection, 8 mice/group were sacrificed by CO2 overdose and the lungs were excised and homogenized in 1 ml PBS. Tenfold serial dilutions were prepared in PBS to enumerate viable bacterial numbers. Samples were inoculated (20 μl) in triplicate onto TSA plates supplemented with 5% horse blood and incubated overnight 37° C. prior to evaluation. Further sets of mice were sacrificed on day 8 post-infection and samples as above.

Analysis of Data

The outcome measure for comparison of treatment was the number of bacteria in the lungs at 3 and 7 day post infection. Results are presented as group means with standard deviations. Statistical analysis was performed using the Students t-test where a value of <0.05 was considered significant.

Results:

72 h Post Infection

Bacterial counts from group 1-4 were significantly lower ($p<0.05$) than those from group 1-3.

Bacterial counts from group 1-4 were significantly lower ($p<0.05$) than those from group 1-5.

168 h Post Infection

Bacterial numbers in all groups were approx 2 logs lower at 8 days than at 3 days, indicating that the infection was resolving.

Bacterial counts from group 1-2 were significantly lower ($p<0.05$) than those from group 1-5.

| | Day 3 | | Day 8 | |
|---|---|---|---|---|
| Group | Log CFU/lung | Standard Deviation | Log CFU/lung | Standard Deviation |
| 1-1 | 6.93 | 0.61 | 5.23 | 1.28 |
| 1-2 | 6.59 | 1.25 | 4.08 | 1.34 |
| 1-3 | 7.09 | 0.8 | 5.32 | 1.26 |

-continued

| | Day 3 | | Day 8 | |
|---|---|---|---|---|
| Group | Log CFU/lung | Standard Deviation | Log CFU/lung | Standard Deviation |
| 1-4 | 6.09 | 1.43 | 4.46 | 2.32 |
| 1-5 | 7.19 | 0.89 | 5.42 | 1.05 |
| 1-6 | 6.68 | 1.14 | 5.01 | 1.48 |

As demonstrated above, anti-polysaccharide antibody alone (group 1-5) does not afford protection against growth of pneumococci in the lung. PdB adjuvanted with AlPO4 does not confer protection either, but at day 8 there is a trend to protection when PdB is combined with 3D-MPL (group 1-2).

At Day 3, the group most significantly protected, group 1-4, had all three elements, PdB, 3D-MPL and passively administered anti-polysaccharide antibody. This conclusion is supported by the mortality rate. Group 1-4 had only 2/8 deaths compared to 5/10 for groups 1-5 and 1-3.

Conclusion:

As the experiment was done with passively immunised animals, the synergistic effect of also actively immunising with pneumolysin and MPL cannot be due to an increase in the level of antibodies against the polysaccharide antigen.

As the animals were only passively immunised against pneumococcal polysaccharide, by day 8 levels of such antibody would have largely dissipated from the host.

Even so, significant protection against pneumococcal pneumonia could be seen in groups immunised with pneumolysin plus 3D-MPL and especially in groups immunised with pneumolysin plus 3D-MPL plus passively administered anti-polysaccharide antibody, indicating the synergy of this combination.

If the anti-polysaccharide immunisation had been carried out actively (preferably with conjugated polysaccharide), the effect would have been even more marked, as the effect of B-cell memory, and constant levels of anti-PS antibody would have contributed to the immune response cooperation (see for example FIG. 1C where many of the animals actively immunised with polysaccharide and protein was shown to have no bacteria in the lungs after challenge).

Example 6

Immunogenicity in 1-Year-Old Balb/C mice of 11-Valent Pneumococcal-Polysaccharide Protein D Conjugate Vaccine Adjuvanted with 3D-MPL Introduction & Objective(s):

Protection against pneumococcal infection is mediated by serotype specific antibody through opsonophagocytosis. It may be surmised that increases in the antibody concentration will result in greater protection, and therefore much effort has been expended to find ways to increase the humoral response. One strategy that has been applied successfully to conjugate vaccines in pre-clinical studies is the use of immunostimulating adjuvants (reviewed in Poolman et al. 1998, Carbohydrate-Based Bacterial Vaccines. In: Handbook of Experimental Pharmacology eds. P. Perlmann and H. Wigsell. Springer-Verlag, Heidelberg, D).

The data presented in this section show the results of the latest experiment using clinical lots in a protocol designed to mimic a clinical trial.

Protocol:

One-year-old balb/c mice were immunised with ¹/₁₀th of the human dose of pneumococcal-polysaccharide protein D conjugate vaccine, or 23-valent plain polysaccharide vaccine. The vaccines used were clinical lots DSP009, DSP013 or DSP014 corresponding to the 1 mcg dosage of serotypes 6B and 23F and 5 mcg of the remaining serotypes of the 11-valent conjugated vaccine, the 0.1 mcg dosage of the 11-valent conjugated vaccine, or the 0.1 mcg dosage of the 11-valent conjugated vaccine adjuvanted with 5 mcg 3D-MPL, respectively. All 11-valent conjugated vaccines were also adjuvanted with 50 µg AlPO4.

Groups of 20 mice were immunised intramuscularly. Injections of the groups listed in the following table were performed on days 0 and 21. Test bleeds were obtained on day 35, (14 days after the second dose).

TABLE

Immunisation Schedule for 1-year-old Balb/c mice immunised with clinical lots of pneumococcal-polysaccharide Protein D conjugate vaccine.

| Group | Day 0 Vaccine Dose 1 | Day 21 Vaccine Dose 2 | Number of mice |
|---|---|---|---|
| 1 | PNEUMOVAX ®-23 2.5 mcg | Buffer | 20 |
| 2a | 11-valent Pn-PD 0.1 mcg | Buffer | 20 |
| 2b | 11-valent Pn-PD 0.1 mcg | 11-valent Pn-PD 0.1 mcg | 20 |
| 3a | 11-valent Pn-PD + MPL 0.1 mcg + 5 mcg | Buffer | 20 |
| 3b | 11-valent Pn-PD + MPL 0.1 mcg + 5 mcg | 11-valent Pn-PD + MPL 0.1 mcg + 5 mcg | 20 |
| 4a | 11-valent Pn-PD 1/0.5 mcg | Buffer | 20 |
| 4b | 11-valent Pn-PD 1/0.5 mcg | 11-valent Pn-PD 1/0.5 mcg | 20 |
| Control | Buffer | Buffer | 20 |

The sera were tested by ELISA for IgG antibodies to the pneumococcal polysaccharides following the CDC/WHO consensus protocol, that is, after neutralisation of the sera with cell-wall polysaccharide. The ELISA was calibrated to give antibody concentrations in mcg/ml using serotype specific IgG1 monoclonal antibodies.

Statistical analyses of comparisons were calculated using UNISTAT® version 5.0 beta. ANOVA by the Tukey-HSD method was performed on log transformed IgG concentrations. Pairwise comparison of seroconversion rates was performed using Fisher's exact test.

Results:

The GMC IgG and 95% confidence interval against the 11 serotypes and protein D induced 14 days after the second immunisation (dose 2) are shown in the following table. Seroconversion rates are shown where a 95% confidence interval could not be calculated.

Group 1 shows the effect of immunisation with plain polysaccharides, which normally induce only IgM in animals. Most IgG levels are below the threshold of detection; nevertheless, balb/c mice were able to make IgG to a few pneumococcal polysaccharides, notably serotypes 3, 19F and 14.

Immunisation with conjugate vaccines induced IgG antibody with high seroconversion rates against all serotypes except 23F.

A dosage-dependent response (group 4 vs group 2) was observed only for serotypes 7F and 19F, but these observations were not statistically significant. A greater response was observed after two doses (b groups vs a groups) for serotypes 3, 6B, 7F and 19F, and PD, and these observations were statistically significant in many cases with all 3 formulations.

Most interesting is the effect of 3D-MPL. Two doses of the 3D-MPL formulated vaccine (group 3b) induced the highest GMC of specific IgG, and this was statistically significant for all serotypes except 23F, in which case it had a significantly higher seroconversion rate (p=0.02 group 3b vs 2b, Fisher's exact).

TABLE

Geometric Mean [IgG] and 95% Confidence Intervals to Selected Pneumococcal Serotypes and Protein D in 1-Year-Old Balb/c 14 days Post II Immunisation with 11-valent PS-PD Conjugate Vaccine

| Sero-type | Group | | | | | | |
|---|---|---|---|---|---|---|---|
| | 1 GM [IgG] µg/ml (95% CI) | 2a GM [IgG] µg/ml (95% CI) | 2b GM [IgG] µg/ml (95% CI) | 3a GM [IgG] µg/ml (95% CI) | 3b GM [IgG] µg/ml (95% CI) | 4a GM [IgG] µg/ml (95% CI) | 4b GM [IgG] µg/ml (95% CI) |
| 3 | 0.24 (0.16-0.6) | 0.18 (0.11-0.27) | 0.84 (0.47-1.5) | 0.72 (0.51-1.0) | 4.84 (3.0-7.9) | 0.22 (0.14-0.35) | 0.95 (0.19-1.8) |
| 6B | 0.02 0/20# | 0.04 8/19 | 0.19 (0.09-0.41) | 0.14 (0.07-0.27) | 0.74 (0.29-1.9) | 0.09 (0.05-0.16) | 0.11 (0.05-0.23) |
| 7F | 0.04 0/20# | 0.07 (0.04-0.12) | 0.19 (0.10-0.39) | 0.15 (0.10-0.22) | 0.97 (0.49-2.0) | 0.09 (0.06-0.14) | 0.45 (0.20-1.02) |
| 14 | 0.15 3/20# | 4.5 (2.5-8.1) | 6.2 (3.6-10.5) | 12.9 (7.8-21.2) | 13.6 (9.4-19.7) | 4.0 (2.0-8.0) | 6.9 (4.6-10.6) |
| 19F | 1.2 (0.56-2.6) | 6.7 (3.6-12.5) | 12.1 (7.6-19.3) | 10.1 (5.5-18.5) | 58.5 (42-81) | 5.9 (3.5-9.9) | 22.0 (16.0-30.2) |
| 23F | 0.07 1/20# | 0.08 3/20# | 0.08 2/19# | 0.07 2/10# | 0.17 9/20# | 0.06 1/18# | 0.10 4/20# |
| PD* | 0.25 1/20# | 5.2 (3.3-8.3) | 11.9 (6.9-20.7) | 13.5 (9.5-19.0) | 98.0 (49.1-195.) | 10.9 (6.4-18.4) | 38.7 (21.3-70.3) |

*In EU/ml;
Seroconversion rate, defined as 2 standard deviations above the average of the negative control.
Please refer to previous table for group definitions.

Conclusion:

The data presented here demonstrates that the addition of 3D-MPL to the 11-valent pneumococcal-polysaccharide Protein D conjugate vaccine increased the immune response in elderly balb/c mice to all serotypes tested.

In most cases, two doses of vaccine induced higher geometric mean IgG concentrations that one dose. Since this is not observed using plain polysaccharide vaccine, even in humans, it is considered an indication of a T-cell dependent immune response and the induction of immune memory.

These data support a vaccine administration scheme using conjugated pneumococcal polysaccharides adjuvanted with Th1 adjuvants (preferably 3D-MPL), whereby at least two doses of the adjuvanted vaccine are administered, preferably 1-12 weeks apart, and most preferably 3 weeks apart. Such an administration scheme is considered a further aspect of the invention.

The mice used in the experiment were non-responsive to PS 23 (plain or conjugated). Interestingly, although antibody levels against the polysaccharide remained low regardless of the vaccine composition used, many more mice responded to PS 23 when 3D-MPL was used as the adjuvant (the seroconversion being significantly higher). A use of Th1 adjuvants, particularly 3D-MPL, in vaccine compositions comprising conjugated pneumococcal polysaccharides in order to relieve non-responsiveness to a pneumococcal polysaccharide in a vaccinee is a still further aspect of the invention. A method of relieving non-responsiveness with the aforementioned composition using the two dose administration scheme described above is yet another aspect.

Example 7

*Neisseria Meningitidis* C Polysaccharide—Protein D Conjugate (PSC-PD)

A: Expression of Protein D
  As for Example 1.

B: Manufacture of Polysaccharide C

The source of group C polysaccharide is the strain C11 of *N. meningitidis*. This is fermented using classical fermentation techniques (EP 72513). The dry powder polysaccharides used in the conjugation process are identical to MENCEVAX™ (SB Biologicals s.a.).

An aliquot of C11 strain is thawed and 0.1 ml of suspension is streaked on one Mueller Hinton medium petri dish supplemented with yeast extract dialysate (10%, v/v) and incubated for 23 to 25 hrs at 36° C. in a water saturated air incubator.

The surface growth is then re-suspended in sterilized fermentation medium and inoculated with this suspension on one Roux bottle containing Mueller Hinton medium supplemented with yeast extract dialysate (10%, v/v) and sterile glass beads. After incubation of the Roux bottle during 23 to 25 hrs at 36° C. in a water saturated air incubator, the surface growth is re-suspended in 10 ml sterile fermentation medium and 0.2 to 0.3 ml of this suspension are inoculated onto 12 other Mueller Hinton medium Roux bottles.

After incubation during 23 to 25 hrs at 36° C. in a water saturated air incubator, surface growth is re-suspended in 10 ml sterile fermentation medium. The bacterial suspension is pooled in a conical flask.

This suspension is then aseptically transferred into the fermenter using sterile syringes.

The fermentation of meningococcus is performed in fermenters contained in a clean room under negative pressure. The fermentation is generally completed after 10-12 hrs corresponding to approximately $10^{10}$ bacteria/ml (i.e. the early stationary phase) and detected by pH increase.

At this stage, the entire broth is heat inactivated (12 min at 56° C.) before centrifugation. Before and after inactivation, a sample of the broth is taken and streaked onto Mueller Hinton medium petri dishes.

C: PS Purification

The purification process is a multi-step procedure performed on the entire fermentation broth. In the first stage of purification, the inactivated culture is clarified by centrifugation and the supernatant is recovered.

Polysaccharide purification is based on precipitation with a quaternary ammonium salt (Cetyltrimethylammonium Bromide/CTAB, CETAVLON®). CTAB forms insoluble complexes with polyanions such as polysaccharides, nucleic acid and proteins depending on their pI. Following ionic controlled conditions, this method can be used to precipitate impurities (low conductivity) or polysaccharides (high conductivity).

The polysaccharides included in clarified supernatant are precipitated using a diatomaceous earth (CELITE® 545) as matrix to avoid formation of insoluble inert mass during the different precipitations/purifications.

Purification Scheme for *N. meningitidis* Polysaccharide C:

Step 1: PSC-CTAB complex fixation on CELITE® 545 (diatomaceous earth) and removal of cells debris, nucleic acids and proteins by washing with CTAB 0.05%.

Step 2: Elution of PS with EtOH 50%. The first fractions which are turbid and contain impurities and LPS are discarded. The presence of PS in the following fractions is verified by floculation test.

Step 3: PS-CTAB complex re-fixation on CELITE® 545 (diatomaceous earth) and removal of smaller nucleic acids and proteins by CTAB 0.05% washing.

Step 4: Elution of PS with EtOH 50%. The first turbid fractions are discarded.

The presence of PS in the following fractions is verified by floculation test.

The eluate is filtered and the filtrate containing crude polysaccharide collected. The polysaccharide is precipitated from the filtrate by adding ethanol to a final concentration of 80%. The polysaccharide is then recovered as a white powder, vacuum dried and stored at −20° C.

D: CDAP Conjugation

Conjugation of PSC and PD

For conjugation of PSC and PD, the CDAP conjugation technology was preferred to the classical CNBr activation and coupling via a spacer to the carrier protein. The polysaccharide is first activated by cyanylation with 1-cyano-4-dimethylamino-pyridinium tetrafluoroborate (CDAP). CDAP is a water soluble cyanylating reagent in which the electrophilicity of the cyano group is increased over that of CNBr, permitting the cyanylation reaction to be performed under relatively mild conditions. After activation, the polysaccharide can be directly coupled to the carrier protein through its amino groups without introducing any spacer molecule. The unreacted estercyanate groups are quenched by means of extensive reaction with glycine. The total number of steps involved in the preparation of conjugate vaccines is reduced and most importantly potentially immunogenic spacer molecules are not present in the final product.

Activation of polysaccharides with CDAP introduces a cyanate group in the polysaccharides and dimethylaminopyridine (DMAP) is liberated. The cyanate group reacts with $NH_2$-groups in the protein during the subsequent coupling procedure and is converted to a carbamate.

PSC Activation and PSC-PD Coupling

Activation and coupling are performed at +25° C.

120 mg of PS is dissolved for at least 4 h in WFI.

CDAP solution (100 mg/ml freshly prepared in acetonitrile) is added to reach a CDAP/PS (w/w) ratio of 0.75.

After 1 min 30, the pH is raised up to activation pH (pH 10) by addition of triethylamine and is stabilised up to PD addition.

At time 3 min 30, NaCl is added to a final concentration of 2M.

At time 4 min, purified PD is added to reach a PD/PS ratio of 1.5/1; pH is immediately adjusted to coupling pH (pH 10). The solution is left for 1 h under pH regulation.

Quenching 6 ml of a 2M glycine solution is added to the PS/PD/CDAP mixture. The pH is adjusted to the quenching pH (pH 8.8). The solution is stirred for 30 min at the working temperature, then overnight at +2-8° C. with continuous slow stirring.

PS-PD Purification

After filtration (5 μm), the PS-PD conjugate is purified in a cold room by gel permeation chromatography on a S400HR SEPHACRYL® gel to remove small molecules (including DMAP) and unconjugated PD: Elution—NaCl 150 mM pH 6.5; Monitoring—UV 280 nm, pH and conductivity.

Based on the different molecular size of the reaction components, PS-PD conjugates are eluted first followed by free PD and finally DMAP. Fractions containing conjugate as detected by DMAB (PS) and pBCA (protein) are pooled. The pooled fractions are sterile filtered (0.2 μm)

E: Formulation of PSC-PD Adsorbed Conjugate Vaccine

Washing of $AlPO_4$

In order to optimize the adsorption of PSC-PD conjugate on $AlPO_4$, the $AlPO_4$ is washed to reduce the $PO_4^{3-}$ concentration:

$AlPO_4$ is washed with NaCl 150 mM and centrifuged (4×); the pellet is then resuspended in NaCl 150 mM then filtrated (100 μm); and the filtrate is heat sterilized.

This washed $AlPO_4$ is referred to as WAP (washed autoclaved phosphate).

Formulation Process

The PSC-PD conjugate bulk is adsorbed on AlPO4 WAP before the final formulation of the finished product. $AlPO_4$ WAP was stirred with PSC-PD for 5 minutes at room temperature. The pH was adjusted to 5.1, and the mixture was stirred for a further 18 hours at room temperature. NaCl solution was added to 150 mM, and the mixture was stirred for 5 minutes at room temperature. 2-phenoxyethanol was added to 5 mg/mL and the mixture was stirred for 15 minutes at room temperature, then adjusted to pH 6.1.

Final Composition/Dose

| | |
|---|---|
| PSC-PD: | 10 μg PS |
| AlPO4 WAP: | 0.25 mg $Al^{3+}$ |
| NaCl: | 150 mM |
| 2-phenoxy-ethanol: | 2.5 mg |
| Water for Injection: | to 0.5 ml |
| pH: | 6.1 |

F: Preclinical Information

Immunogenicity of Polysaccharide Conjugate in Mice

The immunogenicity of the PSC-PD conjugate has been assessed in 6- to 8-weeks-old Balb/C mice. The plain (unadsorbed) conjugate or the conjugate adsorbed onto AlPO4 was injected as a monovalent vaccine. Anti-PSC antibodies induced were measured by ELISA whilst functional antibodies were analysed using the bactericidal test, both methods being based on the CDC (Centers for Disease Control and Prevention, Atlanta, USA) protocols. Results from two different experiments performed to assess the response versus the dose and adjuvant (AlPO$_4$) effect are presented.

Dose-Range Experiment

In this experiment, the PSC-PD was injected twice (two weeks apart) in Balb/C mice. Four different doses of conjugate formulated on AlPO4 were used: 0.1; 0.5; 2.5; and 9.6 μg/animal. The mice (10/group) were bled on days 14 (14 Post I), 28 (14 Post II) and 42 (28 Post II). Geometric mean concentrations (GMCs) of polysaccharide C specific antibodies measured by ELISA were expressed in μg IgG/ml using purified IgG as reference. Bactericidal antibodies were measured on pooled sera and titres expressed as the reciprocal of the dilution able to kill 50% of bacteria, using the *N. meningitidis* C11 strain in presence of baby rabbit complement.

The dose-response obtained shows a plateau from the 2.5 μg dose. Results indicate that there is a good booster response between 14 Post I and 14 Post II. Antibody levels at 28 Post II are at least equivalent to those at 14 Post II. Bactericidal antibody titres are concordant with ELISA concentrations and confirm the immunogenicity of the PSC-PD conjugate.

Effect of Adjuvant

In this experiment, one lot of PSC-PD conjugate formulated on AlPO4 was assessed, the plain (non-adjuvanted) conjugate was injected for comparison. 10 mice/group were injected twice, two weeks apart, by the subcutaneous route, with 2 μg of conjugate. Mice were bled on days 14 (14 Post I), 28 (14 Post II) and 42 (28 Post II), and ELISA and functional antibody titres measured (only on 14 Post II and 28 Post II for the bactericidal test). The AlPO4 formulation induces up to 10 times higher antibody titres as compared to the non-adjuvanted formulations.

Conclusions

The following general conclusions can be made from the results of the experiments described above:

PSC-PD conjugate induces an anamnestic response demonstrating that PSC, when conjugated, becomes a T cell dependent antigen.

Anti-PSC antibody concentrations measured by ELISA correlate well with bactericidal antibody titres showing that antibodies induced by the PSC-PD conjugate are functional against *N. meningitidis* serogroup C.

Approximately 2.5 μg of conjugate adsorbed onto AlPO4 appears to elicit an optimum antibody response in mice.

The CDAP chemistry appears to be a suitable method for making immunogenic PSC-PD conjugates.

Example 8

Preparation of a Polysaccharide from *N. meningitidis* Serogroup A—PD Conjugate

A dry powder of polysaccharide A (PSA) is dissolved for one hour in NaCl 0.2 M solution to a final concentration of 8 mg/ml. pH is then fixed to a value of 6 with either HCl or NaOH and the solution is thermoregulated at 25° C. 0.75 mg CDAP/mg PSA (a preparation to 100 mg/ml acetonitrile) is added to the PSA solution. After 15 minutes without pH regulation, NaOH 0.2 M is added to obtain a pH of 10. 2 5 minutes later, protein D (concentrated to 5 mg/ml) is added according to a PD/PSA ratio of approximately 1. A pH of 10 is maintained during the coupling reaction period of 1 hour. Then, 10 mg glycine (2 M pH 9.0)/mg PSA is added and pH regulated at a value of 9.0 for 30 minutes at 25° C. The mixture is then conserved overnight at 4° C. before purification by exclusion column chromatography (SEPHACRYL® S400HR from Pharmacia). The conjugate elutes first followed by unreacted PD and by-product (DMAP, glycine, salts). The conjugate is collected and sterilized by a 0.2 μm filtration on a SARTOPORE® membrane from Sartorius.

Example 9

In Vitro Characterisations of the Products of Examples 7 and 8

The major characteristics are summarized in the table here below:

| Conjugate N° description | Protein and PS content (μg/ml) | PS/protein ratio (w/w) | Free Protein (%) | Free PS (%) |
|---|---|---|---|---|
| 1 PS C - PD NaOH for pH regulation | PD: 210 PS: 308 | 1/0.68 | <2 | 8-9 |
| 2 PS C - PD TEA for pH regulation | PD: 230 PS: 351 | 1/0.65 | <2 | 5-6 |
| 3 PS A - PD NaOH for pH regulation | PD: 159 PS: 149 | 1/1.07 | 5 | 5-9 |

In vivo Results

Balb/C mice were used as animal model to test the immunogenicity of the conjugates. The conjugates were adsorbed either onto AlPO$_4$ or Al(OH)$_3$ (10 μg of PS onto 500 μg of Al$^{3+}$) or not adsorbed. The mice were injected as followed: 2 injections at two week intervals (2 μg PS/injection).

From these results, we can conclude first that free PS influences greatly the immune response. Better results have been obtained with conjugates having less than 10% free PS. The above improvements to the CDAP process is thus a further aspect of the invention.

The formulation is also important. AlPO$_4$ appears to be the most appropriate adjuvant in this model. The conjugates induce a boost effect which is not observed when polysaccharides are injected alone.

Conclusions

Conjugates of *N. meningitidis* A and C were obtained with a final PS/protein ratio of 1 and 0.6-0.7 (w/w) respectively. Free PS and free carrier protein were below 10% and 15% respectively. Polysaccharide recovery is higher than 70%. Conjugates of PSA and PSC obtainable by the above improved (optimised) CDAP process (regardless of the carrier protein, but preferably protein D) is thus a further aspect of the invention.

Example 10

Preparation of a Polysaccharide from *H. influenzae* b—PD Conjugate

*H. influenzae* b is one of the major causes of meningitis in children under 2 years old. The capsular polysaccharide of *H. influenzae* (PRP) as a conjugate onto tetanus toxoid is well known (conjugated by chemistry developed by J. Robbins). CDAP is an improved chemistry. The following is account of optimal CDAP conditions found for conjugating PRP, preferably to PD.

The parameters influencing the reaction of conjugation are the following:

The initial concentration of polysaccharide (which can have a double impact on the final levels of free polysaccharide and on the sterile filtration step).

The initial concentration of the carrier protein.

The initial ratio of polysaccharide to protein (which can also have the double impact on the final levels of free polysaccharide and on the sterile filtration step).

The quantity of CDAP used (usually in large excess).

The temperature of the reaction (which can influence the breakdown of the polysaccharide, the kinetics of the reaction, and the breakdown of the reactive groups).

The pH of activation and coupling.

The pH of quenching (influencing the level of residual DMAP).

The time of activation, coupling and quenching.

The present inventors have found that the 3 most critical parameters to optimise the quality of the end product are: the initial ratio of polysaccharide/protein; the initial concentration of polysaccharide; and the coupling pH.

A reaction cube was thus designed with the above 3 conditions as the three axes. The central points (and experimented value range) for these axes were: PS/protein ratio —1/1 (±0.3/1); [PS]=5 mg/ml (±2 mg/ml); and coupling pH=8.0 (±1.0 pH unit).

The less essential parameters were fixed at the following: 30 mg of polysaccharide were used; temperature 25° C.; [CDAP]=0.75 mg/mg PS; pH titrated with 0.2M NaOH; activation pH=9.5; temperature for activation=1.5 minutes; coupling temperature–1 hour; [protein]=10 mg/ml; quench pH=9.0; temperature of quenching=1 hour; temperature of dissolving PS in solvent=1 hour in 2M NaCl; purification on SEPHACRYL® S-400HR eluted with NaCl 150 mM at 12 cm/hour; and filter sterilising with a SARTOLAB® P20 at 5 ml/min.

The data looked at to establish optimised conditions when making products within the aforementioned reaction cube were: process data—maximum yield after filtration, maximum level of protein incorporated; and quality of product data—final ratio PS/protein, level of free PS, level of free protein, minimum levels of residual DMAP (a breakdown product of CDAP).

Output from Filtration

The factor which affects the output after filtration is the interaction between the initial [PS] and the coupling pH and initial PS/protein ratio. At low [PS] there is little interaction with the latter 2 factors, and good filterability always results (approx. 95% for all products). However, at high concentrations filterability diminishes if the pH and the initial ratio increase (high [PS], lowest ratio, lowest pH=99% filtration; but high [PS], highest ratio and pH=19% filtration).

Level of Incorporation of the Protein

The ratio of the final ratio PS/protein with respect to the initial ratio is a measure of the efficiency of coupling. At high [PS], pH does not effect the ratio of ratios. However the initial ratio does (1.75 at low initial ratio, 1.26 at high initial ratios). At low [PS], the ratio of ratios is for the most part lower, however pH now has more of an affect (low pH, low ratio=0.96; low pH, high ratio=0.8; high pH, low ratio=1.4; and high pH, high ratio=0.92).

Final PS/Protein Ratio

The final ratio depends on the initial ratio and the [PS]. The most sizeable final ratios are obtained with a combination high initial ratios and high [PS]. The effect of pH on the final ratio is not as significant as a weak [PS].

Level of Free Protein D

The least amounts of free protein D is observed at high pH and high [PS] (levels approaching 0.0). The effect of high [PS] becomes especially marked when pH is low. The raising of the initial ratio contributes a little bit to the increase in free protein D.

Residual DMAP

The initial ratio does not have a significant effect. In contrast, the level of DMAP increases with the [PS], and decreases when the pH is raised.

Conclusions

The most preferable conjugation conditions are thus the following: coupling pH=9.0; [PS]=3 mg/ml; and initial ratio=1/1. With such conditions the characteristics of the final product are as follows:

| Final ratio PS/protein | | PS Output from filtration (%) | | Ratio of ratios | | Free protein D (%) | | DMAP levels (ng/10 μg PS) | |
|---|---|---|---|---|---|---|---|---|---|
| value | range | value | Range | value | Range | value | range | value | range |
| 1.10 | 0.91-1.30 | 92.6 | 50-138 | 1.16 | 1.03-1.29 | 0.71 | 0-10.40 | 4.95 | 2.60-7.80 |

Conjugates of PRP obtainable by the above improved (optimised) CDAP process (regardless of the carrier protein, but preferably protein D) is thus a further aspect of the invention.

Example 11

Protein D as an Antigen—how its Protective Efficacy Against Non-Typeable *H. influenzae* can be Improved by Formulating it with 3D-MPL Female Balb/c Mice (10 per group) were immunized (intramuscularly) with the eleven valent pneumococcal polysaccharide-protein D conjugate vaccine for a first time at the age of 20 weeks (D0) and received a second immunization two weeks later (D14). Blood was collected 7 days after the second immunization. Antibody titres against protein D were measured in terms of the quantity of IgG1, IgG2a and IgG2b type antibodies.

Freeze-dried undecavalent vaccines (without $AlPO_4$) were prepared by combining the conjugates with 15.75% lactose, stirring for 15 minutes at room temperature, adjusting the pH to 6.1±0.1, and lyophilising (the cycle usually starting at −69° C., gradually adjusting to −24° C. over 3 hours, then retaining this temperature for 18 hours, then gradually adjusting to −16° C. over 1 hour, then retaining this temperature for 6 hours, then gradually adjusting to +34° C. over 3 hours, and finally retaining this temperature over 9 hours).

Composition of formulations and reconstituants for lyophilisates are presented in Table 13.

The most characteristic measurement as to whether a Th1-type cell mediated immune response has occurred is known to be correlated with the level of IgG2a antibody. As can be seen from the data, a surprisingly large increase in IgG2a results if the protein D has been lyophilised with a Th1 adjuvant (in this case 3D-MPL).

TABLE 13

Composition of formulations (per human dose), and antibody titres against protein D in mice (with 1/10 dose)

| Physical state | PS (/500 µl) | AlPO$_4$ (/500 µl) | Immuno-stimulant | Caking agent | Preservative | Reconstituant | IgG1 | IgG2a µg/ml | IgG2b | IgG1 | IgG2a % | IgG2b |
|---|---|---|---|---|---|---|---|---|---|---|---|---|
| liquid | 1 µg | 500 µg | no | no | 2-PE[3] | no | 76 | 0.425 | 0.24 | 99.1 | 0.554 | 0.313 |
| liquid | 5 µg | 500 µg | no | no | 2-PE | no | 66 | 0.284 | 0.176 | 99.3 | 0.427 | 0.265 |
| liquid | 1 µg | 0 µg | no | no | 2-PE | no | 6.6 | 0.207 | 0.036 | 96.4 | 3.02 | 0.526 |
| liquid | 5 µg | 0 µg | no | no | 2-PE | no | 5.2 | 0.169 | 0.043 | 96.1 | 3.12 | 0.795 |
| freeze-dried | 1 µg | 0 µg | no | lactose 3.15% | no | NaCl 150 mM[1] | 5.2 | 0.147 | 0.046 | 96.4 | 2.73 | 0.853 |
| freeze-dried | 5 µg | 0 µg | no | lactose 3.15% | no | NaCl 150 mM[1] | 11.1 | 0.11 | 0.168 | 97.6 | 0.967 | 1.477 |
| freeze-dried | 1 µg | 0 µg | no | lactose 3.15% | no | AlPO$_4$ 500 µg[2] | 45 | 1.86 | 0.075 | 95.9 | 3.96 | 0.160 |
| freeze-dried | 5 µg | 0 µg | no | lactose 3.15% | no | AlPO$_4$ 500 µg[2] | 19 | 0.077 | 0.119 | 99.0 | 0.401 | 0.620 |
| freeze-dried | 1 µg | 0 µg | no | lactose 3.15% | no | MPL 50 µg[1] | 45 | 2.6 | 3.5 | 88.1 | 5.09 | 6.849 |
| freeze-dried | 5 µg | 0 µg | no | lactose 3.15% | no | MPL 50 µg[1] | 135 | 25 | 5.1 | 81.8 | 15.1 | 3.089 |
| freeze-dried | 1 µg | 0 µg | MPL (50 µg) | lactose 3.15% | no | buffer[1] | 43 | 22 | 5.7 | 60.8 | 31.1 | 8.062 |
| liquid | 1 µg | 500 µg | MPL (50 µg) | no | 2-PE | no | 441 | 7.1 | 9.1 | 96.5 | 1.55 | 1.990 |
| liquid | 5 µg | 500 µg | MPL (50 µg) | no | 2-PE | no | 299 | 1.4 | 0.899 | 99.2 | 0.465 | 0.298 |

[1] before injection;
[2] +/−2 hours before injection;
[3] 2-phenoxyethanol

The invention claimed is:

1. A multivalent immunogenic composition comprising isolated capsular polysaccharides of at least four serotypes of *Streptococcus pneumoniae*, each of said isolated capsular polysaccharides conjugated to an isolated protein D from *Haemophilus influenzae* that lacks a leader peptide and the N-terminal cysteine and contains a T-helper epitope, wherein the protein D is not lipidated.

2. The immunogenic composition of claim 1 additionally comprising an adjuvant.

3. The immunogenic composition of claim 2, wherein said capsular polysaccharides conjugated to the protein D are adsorbed onto the adjuvant, wherein the adjuvant is aluminum phosphate.

4. The immunogenic composition of claim 1 additionally comprising an isolated pneumolysin.

5. The immunogenic composition of claim 1, wherein the capsular polysaccharides are from serotypes 6B, 18C, 19F and 23F of *Streptococcus pneumoniae*.

6. The immunogenic composition of claim 1, wherein the capsular polysaccharides are from serotypes 4, 6B, 9V, 14, 18C, 19F and 23F of *Streptococcus pneumoniae*.

7. The immunogenic composition of claim 1, wherein the capsular polysaccharides are from serotypes 1, 3, 4, 5, 6B, 7F, 9V, 14, 18C, 19F and 23F of *Streptococcus pneumoniae*.

8. A multivalent immunogenic composition comprising:
(a) isolated capsular polysaccharides of at least four serotypes of *Streptococcus pneumoniae*, each of said isolated capsular polysaccharides conjugated to an isolated protein D from *Haemophilus influenzae* that lacks a leader peptide and the N-terminal cysteine and contains a T-helper epitope, wherein the protein D is not lipidated and
(b) isolated pneumolysin of *Streptococcus pneumoniae*.

9. The immunogenic composition of claim 8 additionally comprising an adjuvant.

10. The immunogenic composition of claim 9, wherein said capsular polysaccharides conjugated to the protein D are adsorbed onto the adjuvant, wherein the adjuvant is aluminum phosphate.

11. The immunogenic composition of claim 8, wherein the pneumolysin is detoxified.

12. The immunogenic composition of claim 8, wherein the capsular polysaccharides are from serotypes 1, 3, 4, 5, 6B, 7F, 9V, 14, 18C, 19F and 23F of *Streptococcus pneumoniae*.

* * * * *

```
                        SEQUENCE LISTING

<160> NUMBER OF SEQ ID NOS: 1

<210> SEQ ID NO 1
<211> LENGTH: 13
<212> TYPE: PRT
<213> ORGANISM: Haemophilus influenzae

<400> SEQUENCE: 1

Met Asp Pro Ser Ser His Ser Ser Asn Met Ala Asn Thr
1               5                   10
```